US012758550B2

(12) United States Patent
Profy et al.

(10) Patent No.: US 12,758,550 B2

(45) Date of Patent: Oct. 13, 2026

(54) TREATMENT OF DIABETIC NEPHROPATHY WITH AN sGC STIMULATOR

(71) Applicant: Cyclerion Therapeutics, Inc., Cambridge, MA (US)

(72) Inventors: Albert Thomas Profy, Cambridge, MA (US); John P. Hanrahan, Cambridge, MA (US)

(73) Assignee: Cyclerion Therapeutics, Inc., Cambridge, MA (US)

( * ) Notice: Subject to any disclaimer, the term of this patent is extended or adjusted under 35 U.S.C. 154(b) by 898 days.

(21) Appl. No.: 17/773,274

(22) PCT Filed: Oct. 28, 2020

(86) PCT No.: PCT/US2020/057741

§ 371 (c)(1),
(2) Date: Apr. 29, 2022

(87) PCT Pub. No.: WO2021/086967

PCT Pub. Date: May 6, 2021

(65) Prior Publication Data

US 2024/0165114 A1 May 23, 2024

Related U.S. Application Data

(60) Provisional application No. 62/993,972, filed on Mar. 24, 2020, provisional application No. 62/927,454, filed on Oct. 29, 2019.

(51) Int. Cl.

| | |
|---|---|
| ***A61K 31/506*** | (2006.01) |
| ***A61K 9/00*** | (2006.01) |

(Continued)

(52) U.S. Cl.

CPC .......... *A61K 31/506* (2013.01); *A61K 9/0053* (2013.01); *A61K 31/155* (2013.01); (Continued)

(58) Field of Classification Search

None

See application file for complete search history.

(56) References Cited

U.S. PATENT DOCUMENTS

2016/0375022 A1* 12/2016 Nakai .................. C07D 401/14
2019/0262340 A1* 8/2019 Kolkhof ............... A61K 31/506

FOREIGN PATENT DOCUMENTS

WO 2017/095697 A1 6/2017
WO 2019/055859 A1 3/2019

OTHER PUBLICATIONS

Clinical Study ID C1973-203 (A Study to Evaluate the Soluble Guanylate Cyclase (sGC) Stimulator IW-1973 in Diabetic Nephropathy/ Diabetic Kidney Disease as Measured by Albuminuria; version 2: Jan. 3, 2018).*

(Continued)

*Primary Examiner* — Bong-Sook Baek

(74) *Attorney, Agent, or Firm* — McCarter & English, LLP; Xin Zhang; Zhongyu "Alex" Wang

(57) ABSTRACT

The present invention relates to a method of treating subjects with diabetic nephropathy by administering certain dosages of Compound I, a stimulator of soluble guanylate cyclase (sGC), either alone or in combination therapy.

(Continued)

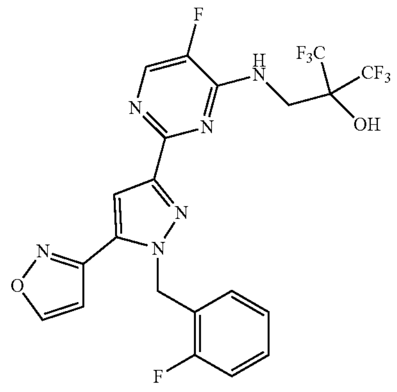

Compound I

18 Claims, 13 Drawing Sheets

(51) Int. Cl.
*A61K 31/155* (2006.01)
*A61K 38/28* (2006.01)
*A61P 3/10* (2006.01)
*A61P 13/02* (2006.01)
*A61P 13/12* (2006.01)

(52) U.S. Cl.
CPC ................ *A61K 38/28* (2013.01); *A61P 3/10* (2018.01); *A61P 13/02* (2018.01); *A61P 13/12* (2018.01)

(56) References Cited

OTHER PUBLICATIONS

Hanrahan et al., Phase 2 Multicenter, Randomized, Double-Blind, Placebo-Controlled Trial to Evaluate the Soluble Guanylate Cyclase Stimulator Praliciguat in Patients with Diabetic Kidney Disease. Diabetes. Jun. 2020; 69(Suppl 1):1073-P.

Profy et al., IW-1973, a Soluble Guanylate Cyclase Stimulator, Inhibits Progression of Diabetic Nephropathy in the ZSF1 Rat Model. Retrieved online at: https://diabetes.diabetesjournals.org/content/66/Supplement_1/A101.article-info. p. A134, Abstract 512-P, Jun. 1, 2017.

International Search Report and Written Opinion for Application No. PCT/US2020/057741, dated Mar. 3, 2021, 10 pages.

Tobin et al., Pharmacological Characterization of IW-1973, a Novel Soluble Guanylate Cyclase Stimulator with Extensive Tissue Distribution, Antihypertensive, Anti-Inflammatory, and Antifibrotic Effects in Preclinical Models of Disease. J Pharmacol Exp Ther. Jun. 2018;365(3):664-675.

* cited by examiner

| Treatment-emergent, Study Drug-related SAE Category | # of patients to trigger DMC review |
|---|---|
| Renal failure (eGFR <15 mL/min/1.73 $m^2$; dialysis or renal transplant indicated) | 2 |
| Spontaneous bleeding events (eg, hemoptysis, subarachnoid or subdural hemorrhage, hematemesis, hematochezia) | 2 |
| Symptomatic hypotension-related events (eg, syncope) | 2 |

DMC=Data Monitoring Committee; eGFR=estimated glomerular filtration rate; SAE=serious adverse event

FIG. 3

| Variable* | Placebo (N = 54) | PRL 20 mg (N = 50) | PRL 40 mg (N = 52) | PRL Combined (N = 102) |
|---|---|---|---|---|
| **UACR (g/kg)** | 1302 (1250) | 1043 (839) | 1100 (891) | 1072 (862) |
| **eGFR (mL/min/1.73m$^2$)** | 49.8 (13.6) | 49.6 (14.2) | 50.7 (14.5) | 50.2 (14.3) |
| % 30-45 | 46 % | 46% | 43% | 44% |
| % >45-60 | 39 % | 42% | 46% | 44% |
| % >60-75 | 15 % | 12 % | 12% | 12% |
| | | | | |
| **Fasting Plasma Glucose (mg/dL)** | 150 (53) | 160 (62) | 167 (83) | 164 (73) |
| **HBA1c (%)** | 7.6 (1.4) | 7.9 (1.4) | 7.9 (1.2) | 7.9 (1.3) |
| | | | | |
| **Systolic Blood Pressure (mmHg)** | 143.0 (17.6) | 138.3 (14.0) | 142.8 (12.8) | 140.6 (13.5) |
| **Mean Arterial Pressure (mmHg)** | 100.6 (11.4) | 96.8 (9.0) | 101.1 (9.1) | 99.0 (9.3) |
| **Heart Rate (bpm)** | 74.4 (10.8) | 73.3 (11.0) | 75.8 (10.5) | 74.6 (10.8) |

*All values are Mean (SD) unless labeled otherwise. Blood pressure, heart rate means by 24-hour ABPM

**PRL = praliciguat

FIG. 4

| Outcome Variable Primary: Weeks 8 & 12 | PBO | PRL 20 mg | PRL 40 mg | PRL Combined |
|---|---|---|---|---|
| Within Group Geometric Mean % Change UACR from Baseline (90% Confidence Interval) | -14.8% (-27, +0.4) | -28.4% (-39, -15) | -27.3% (-39, -13) | -27.8% (-36, -18) |
| | | | | |
| Between PRL and PBO Group Geometirc Mean % Change UACR from Baseline (90% Confidence Interval) | | -16.0% (-33, +6) | -14.6% (-33, +8) | -15.3% (-31, +4) |
| | | | | |
| P Value of Change from PBO | | 0.214 | 0.272 | 0.174 |

FIG. 5

| Outcome Variable Week 12 | PBO | PRL 20 mg | PRL 40 mg | PRL Combined |
|---|---|---|---|---|
| Within Group Geometric Mean % Change UACR from Baseline (90% Confidence Interval) | -14.8%<br>(-31, +6) | -35.2%<br>(-48, -19) | -26.4%<br>(-42, -7) | -30.9%<br>(-41, -19) |
| | | | | |
| Between PRL and PBO Group Geometric Mean % Change UACR from Baseline (90% Confidence Interval) | | -23.9%<br>(-44, +3) | -13.6%<br>(-37, +18) | -18.9%<br>(-38, +6) |
| | | | | |
| P Value of Change from PBO | | 0.141 | 0.446 | 0.196 |

FIG. 6

| **Outcome Variable Mean Arterial BP (24-Hour ABPM)** | **PBO** | **PRL 20 mg** | **PRL 40 mg** | **PRL Combined** |
|---|---|---|---|---|
| Baseline Mean Values (mmHg) | 101 | 96 | 100 | 98 |
| | | | | |
| Within Group LS Mean Change from Baseline 24-hour MAP at Week 12 *(90% Confidence Interval)* | 0.345<br>(-1.6, 2.3) | -3.62<br>(-5.7, -1.6) | -3.23<br>(-5.4, -1.3) | -3.43<br>(-5.0, -1.8) |
| | | | | |
| Between PRL and PBO Group LS Mean Change 24-hour MAP from Baseline at week 12 *(90% Confidence Interval)* | | -3.96<br>(-6.7, -1.3) | -3.58<br>(-6.33, -0.83) | -3.77<br>(-6.09, -1.45) |
| | | | | |
| P Value of Change from PBO | | 0.016 | 0.033 | 0.008 |

FIG. 7

| **Outcome Variable Systolic BP (24-Hour ABPM)** | **PBO** | **PRL 20 mg** | **PRL 40 mg** | **PRL Combined** |
|---|---|---|---|---|
| Baseline Mean Values (mmHg) | 144 | 137 | 141 | 139 |
| | | | | |
| Within Group LS Mean Change from Baseline 24-hour SBP at Week 12 *(90% Confidence Interval)* | -0.12<br>(-2.9, 2.7) | -4.18<br>(-7.1, -1.2) | -4.41<br>(-7.6, -1.3) | -4.30<br>(-6.6, -2.0) |
| | | | | |
| Between PRL and PBO Group LS Mean Change 24-hour from Baseline 24-hour SBP at Week 12 *(90% Confidence Interval)* | | --4.06<br>(-7.9, -0.2) | -4.29<br>(-8.2, -0.34) | -4.17<br>(-7.5, -0.84) |
| | | | | |
| P Value of Change from PBO | | 0.083 | 0.075 | 0.040 |

FIG. 8

| **Outcome Variable Fasting Plasma Glucose** | **PBO** | **PRL 20 mg** | **PRL 40 mg** | **PRL Combined** |
|---|---|---|---|---|
| Baseline Median Value (mg/dL) | 135 | 148 | 164 | 153 |
| | | | | |
| Within Group LS Mean Change from Baseline at Week 12 *(90% Confidence Interval)* | 3.77 (-9.2, 16.7) | 6.09 (-7.1, 19.2) | -14.4 (-28.4, -0.38) | -4.1 (-14.1, 5.7) |
| | | | | |
| Between PRL and PBO Group LS Mean Change from Baseline at week 12 *(90% Confidence Interval)* | | 2.3 (-15.6, 20.2) | -18.2 (-36.7, 0.4) | -7.9 (-23.6, 7.8) |
| | | | | |
| P Value of Change from PBO | | 0.83 | 0.11 | 0.41 |

FIG. 9

| **Outcome Variable Hemoglobin A1c** | **PBO** | **PRL 20 mg** | **PRL 40 mg** | **PRL Combined** |
|---|---|---|---|---|
| Baseline Median Values (%) | 7.00 | 7.500 | 7.85 | 7.50 |
| | | | | |
| Within Group LS Mean Change from Baseline at Week 12 *(90% Confidence Interval)* | -0.08<br>(-0.27, 0.12) | -0.26<br>(-0.51, 0.11) | -0.38<br>(-0.59, -0.18) | -0.34<br>(-0.49, -0.20) |
| | | | | |
| Between PRL and PBO Group LS Mean Change from Baseline at week 12 *(90% Confidence Interval)* | | 0.23<br>(-0.50, +0.04) | 0.30<br>(-0.58, -0.03) | 0.27<br>(-0.50, -0.03) |
| | | | | |
| P Value of Change from PBO | | 0.161 | 0.071 | 0.062 |

FIG. 10

| Outcome Variable Serum Cholesterol | PBO | PRL 20 mg | PRL 40 mg | PRL Combined |
|---|---|---|---|---|
| Baseline Median Values (mg/dL) | 162 | 179 | 162 | 171 |
| | | | | |
| Within Group LS Mean Change from Baseline at Week 12 *(90% Confidence Interval)* | 4.4<br>(-3.3, 12.0) | -7.8<br>(-15.6, 0.2) | -3.7<br>(-11.9, 4.5) | -5.8<br>(-11.7, +0.3) |
| | | | | |
| Between PRL and PBO Group LS Mean Change from Baseline at week 12 *(90% Confidence Interval)* | | -12.1<br>(-22.7, -1.6) | -8.1<br>(-18.7, +2.6) | -10.1<br>(-19.2, -1.0) |
| | | | | |
| P Value of Change from PBO | | 0.059 | 0.215 | 0.069 |

FIG. 11

| **Outcome Variable Serum LDL Cholesterol** | **PBO** | **PRL 20 mg** | **PRL 40 mg** | **PRL Combined** |
|---|---|---|---|---|
| Baseline Median Values (mg/dL) | 81.0 | 94.9 | 83.5 | 89.6 |
| | | | | |
| Within Group LS Mean Change from Baseline at Week 12 *(90% Confidence Interval)* | 2.9 (-3.5, 9.3) | -6.0 (-12.4, +0.5) | -3.3 (-10.1, 3.5) | -4.6 (-9.5, +0.3) |
| | | | | |
| Between PRL and PBO Group LS Mean Change from Baseline at week 12 *(90% Confidence Interval)* | | -8.9 (-17.5, -0.2) | -6.2 (-15.1, 2.7) | -7.5 (-15.1, +0.5) |
| | | | | |
| P Value of Change from PBO | | 0.093 | 0.253 | 0.102 |

FIG. 12

TREATMENT OF DIABETIC NEPHROPATHY WITH AN sGC STIMULATOR

CROSS REFERENCE TO RELATED APPLICATIONS

This application is a 35 U.S.C. § 371 national stage filing of International Application No. PCT/US2020/057741, filed on Oct. 28, 2020, which in turn claims the benefit of the filing date, under 35 U.S.C. § 119(e), of U.S. Provisional Application No. 62/927,454, filed on Oct. 29, 2019 and U.S. Provisional Application No. 62/993,972, filed on Mar. 24, 2020. The entire contents of each of these applications are incorporated herein by reference.

FIELD OF THE INVENTION

This disclosure relates to a method of treating subjects with diabetic nephropathy (DN) by administering specific dosage regimens of a stimulator of soluble guanylate cyclase (sGC) either alone or in combination therapy.

BACKGROUND OF THE INVENTION

Diabetic Nephropathy

Diabetic nephropathy (DN), also known as diabetic kidney disease (DKD), is a common and serious microvascular complication of Type 1 and Type 2 diabetes mellitus and is characterized by pathological urinary protein excretion (e.g., albumin excretion), glomerular lesions, hypertension, and progressive loss of renal function.

Diagnosis is based on the presence of albuminuria (urine to albumin creatinine ratio [UACR]>30 mg/g) and/or reduced estimated glomerular filtration rate (eGFR <90 mL/min/1.73 $m^2$) in patients with diabetes (Fineberg D, Jandeleit-Dahm K A, Cooper M E (2013) "Diabetic nephropathy: diagnosis and treatment" *Nat Rev Endocrinol December,* 9(12), pp 713-23.). The Kidney Disease: Improving Global Outcomes (KDIGO) Clinical Practice Guideline (National Kidney Foundation. KDIGO 2012 "Clinical Practice Guideline for the Evaluation and Management of Chronic Kidney Disease" *Kidney International Supplements* 2013, 3(1), pp 1-150) provides a kidney disease classification system and risk-stratifies patients based on levels of albuminuria and eGFR.

DN is the leading cause of end-stage renal disease (ESRD, requiring kidney replacement therapy in the form of dialysis or kidney transplant) in the United States and other industrialized countries. DN is also a major risk factor for serious adverse cardiovascular events as well as the single strongest predictor of mortality in patients with diabetes. An estimated 20% to 40% of patients with diabetes develop DN, with higher rates seen in middle-aged African Americans, Hispanics, and American Indians. The prevalence of DN is increasing in the United States and globally with the increasing prevalence of diabetes. The estimated number of persons in the United States with DN has increased from 3.9 million in 1988-1994 to 6.9 million in 2005-2008.

Current standard of care for DN includes glycemic and blood pressure (BP) control and treatment by pharmacological blockade of the renin-angiotensin-aldosterone system (RAAS) by use of angiotensin-converting enzyme inhibitors (ACEi) and/or angiotensin receptor blockers (ARBs). RAAS inhibitors have been shown in clinical trials to reduce albuminuria and delay progression to ESRD and renal replacement therapy (either dialysis or kidney transplant). However, the current standard of care does not prevent progression to ESRD, and the prevalence of DN has not declined with increased use of RAAS inhibitors and glucose-lowering medications. The burden of caring for DN patients is extremely high for both patients and healthcare systems due to the cost of treating ESRD as well as the strong association of DN with cardiovascular disease. Recently, potential new therapies including sodium glucose cotransporter 2 (SGLT2) inhibitors, glucagon-like peptide-1 (GLP-1) receptor agonists, an endothelin receptor antagonist (ERA) and finerenone (a nonsteroidal antimineralocorticoid) have demonstrated promising effects on renal outcomes in clinical trials, but these agents only slow disease progression and substantial risk remains. As a result, there is still an urgent need for additional therapies for DKD, and in particular, for agents with new mechanisms of action.

SUMMARY OF THE INVENTION

In a first aspect of the invention, disclosed herein is a method of treating DN and related symptoms in a human patient in need thereof, by administering a total oral daily dose of Compound I of between 10 mg and 40 mg to said patient either alone or in combination therapy.

In certain embodiments, the invention disclosed herein is a method of improving albuminuria in patients with diabetes by administering a total oral daily dose of Compound I of between 10 mg and 40 mg to said patient either alone or in combination therapy.

In certain embodiments, the invention disclosed herein is a method of improving albuminuria in patients with diabetes that have a value of eGFR below 45 mL/min/1.73 $m^2$ by administering a total oral daily dose of Compound I of between 10 mg and 40 mg to said patient either alone or in combination therapy.

In certain embodiments, the invention disclosed herein is a method of preserving renal function in patients with diabetes by administering a total oral daily dose of Compound I of between 10 mg and 40 mg to said patient either alone or in combination therapy.

In certain embodiments, the invention disclosed herein is a method of delaying or preventing clinical worsening in patients with DN by administering a total oral daily dose of Compound I of between 10 mg and 40 mg to said patient either alone or in combination therapy.

In certain embodiments, the invention disclosed herein is a method of increasing survival in patients with DN by administering a total oral daily dose of Compound I of between 10 mg and 40 mg to said patient either alone or in combination therapy.

In certain embodiments, the invention disclosed herein is a method of improving metabolic parameters in patients with DN by administering a total oral daily dose of Compound I of between 10 mg and 40 mg to said patient either alone or in combination therapy.

In certain embodiments, the invention disclosed herein is a method of reducing the risk of cardiovascular (CV) events in patients with DN by administering a total oral daily dose of Compound I of between 10 mg and 40 mg to said patient either alone or in combination therapy.

In certain embodiments, the invention disclosed herein is a method of improving metabolic outcomes in patients with DN by administering a total oral daily dose of Compound I of between 10 mg and 40 mg to said patient either alone or in combination therapy.

In certain embodiments, the invention disclosed herein is a method of lowering blood pressure in patients with DN by administering a total oral daily dose of Compound I of between 10 mg and 40 mg to said patient either alone or in combination therapy.

In a second aspect of he invention, disclosed herein is the use of Compound I for the manufacture of a medicament for the treatment of DN and related symptoms in a human patient in need thereof, by administering a total oral daily dose of Compound I of between 10 mg and 40 mg to said patient.

In a third aspect of the invention, disclosed herein is a Compound I for use in the treatment of DN and related symptoms in a human patient in need thereof, wherein a total oral daily dose of Compound I of between 10 mg and 40 mg is administered to said patient.

In another aspect of the invention, disclosed herein are methods and uses for the treatment of DN and related symptoms with Compound I in combination therapy with other therapeutic agents.

BRIEF DESCRIPTION OF THE FIGURES

FIG. 1A shows the results for a subpopulation of patients with eGFR between 30 and 45 m/min/1.73 $m^2$ and FIG. 1B shows the results for all patients. These figures display on the Y axis the cumulative % number of patients and, on the X axis, the % changes in UACR from baseline at week 12, for the group given placebo, the group treated with 20 mg of Compound I and the group treated with 40 mg of Compound I.

FIG. 3 is a table showing treatment-emergent, study drug-related serious adverse event categories.

FIG. 4 is a table summarizing the remaining baseline demographic characteristics of the population enrolled in the trial.

FIG. 5 is a table summarizing effects on albuminuria as measured by UACR changes including combined results of weeks 8 and 12.

FIG. 6 is a table summarizing praliciguat treatment effects on albuminuria as measured by UACR changes including results of weeks 8 and 12.

FIG. 7 is a table summarizing praliciguat treatment effects on arterial blood pressure after 12 weeks of treatment.

FIG. 8 is a table summarizing praliciguat treatment effects on systolic blood pressure after 12 weeks of treatment.

FIG. 9 is a table summarizing praliciguat treatment effects on fasting plasma glucose after 12 weeks of treatment.

FIG. 10 is a table summarizing praliciguat treatment effects on hemoglobin A1c after 12 weeks of treatment.

FIG. 11 is a table summarizing praliciguat treatment effects on serum cholesterol after 12 weeks of treatment.

FIG. 12 is a table summarizing praliciguat treatment effects on serum LDL cholesterol after 12 weeks of treatment.

DETAILED DESCRIPTION OF THE INVENTION

Definitions and General Terminology

Figure 1A:
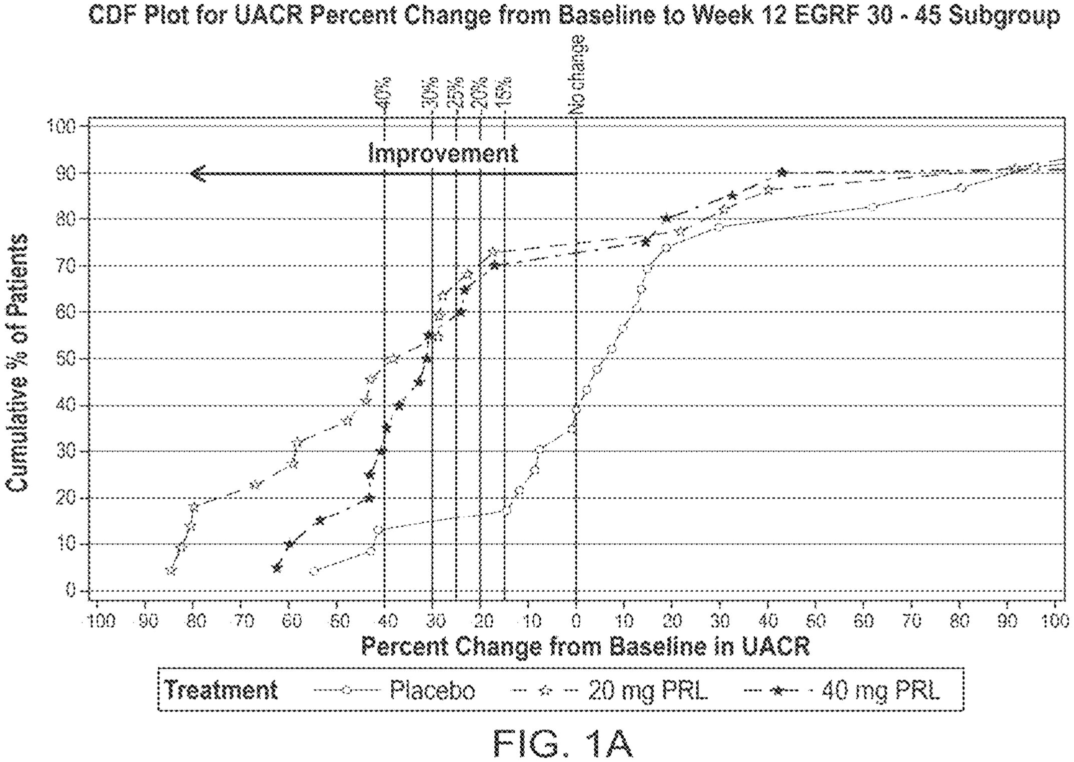
FIGS. 1A and 1B display the results for the primary efficacy outcome measure (change in UACR) in two populations.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will. control.

As used herein, the terms "subject" and "patient" are used interchangeably. A subject or a patient is a human patient or human subject.

For the terms "for example" and "such as," and grammatical equivalences thereof, the phrase "without limitation".or "and without limitation" is understood to follow unless explicitly stated otherwise.

As used herein, "insulin sensitivity" refers to how sensitive the body is to the effects of insulin. Insulin sensitivity can be determined using homeostatic model assessment of insulin resistance (HOMA-IR), which is a method for assessing β-cell function and insulin resistance from basal (fasting) glucose and insulin or C-peptide concentrations. It is also an assessment of the efficiency of peripheral tissue effect of insulin. The normal HOMA-IR value for a healthy human ranges from 0.5 to 1.4. Less than 1.0 means the person is insulin-sensitive which is optimal. A value above 1.9 is indicative of early insulin resistance. A level above 2.9 is indicative of elevated insulin resistance.

The term "therapeutically effective amount" or "pharmaceutically effective amount" as used herein means that amount of active compound or pharmaceutical agent that elicits the medicinal response in a human that is being sought by a medical doctor or other clinician. The therapeutically or pharmaceutically effective amount of a compound is at least the minimum amount necessary to ameliorate, palliate, lessen, delay, reduce, alleviate or cure a disease, disorder or syndrome or one or more of its symptoms, signs or causes. In another embodiment it is the amount needed to bring abnormal levels of certain clinical markers of the disease, disorder or syndrome closer to the normal values or levels. An effective amount can be administered in one or more administrations throughout the day.

The terms "administer" "administering" or "administration" in reference to a compound or pharmaceutical agent, mean introducing the compound into the body of the patient in need of treatment. When Compound I is used in combination with one or more other therapeutic agents, "administration" and its variants are each understood to encompass concurrent and/or sequential introduction of Compound I and the other therapeutic agents into the patient.

The terms "treat", "treating" or "treatment" with regard to a disorder, disease, condition, symptom or syndrome, refer to abrogating or improving the cause and/or the effects (i.e., the symptoms, physiological, physical, psychological, emotional or any other clinical manifestations, observations or measurements, or improving pathological assessments) of the disorder, disease, condition or syndrome. As used herein, the terms "treat", "treatment" and "treating" also refer to the delay or amelioration or prevention of the progression (i.e. the known or expected progression of the disease), severity and/or duration of the disease or delay or amelioration or prevention of the progression of one or more symptoms, clinical manifestations, observations or measurements, or preventing or slowing down the negative progression of pathological assessments (i.e. "managing" without "curing" the condition), resulting from the administration of one or more therapies.

In some embodiments the terms "treat", "treatment" and "treating" refer to the improvement in at least one physiological parameter in a DN patient (e.g. reduction of [UARC], reduction of cholesterol, reduction of plasma glucose, etc.) or improvement of at least one symptom or effect (e.g., reduction of cardiovascular risk).

In other embodiments the terms "treat", "treatment" and "treating" refer to the inhibition or delay of the progression of DN, either physically by, e.g., stabilization of at least one clinically discernible physiological parameter (e.g [UARC]) or stabilization of at lest one measurable symptom of effect (e.g. kidney function, delaying progression towards ESKD).

As used herein, the terms "in combination" (as in the sentence "in combination therapy") or "co-administration" can be used interchangeably to refer to the use of more than one therapy. The use of the terms does not restrict the order in which therapies are administered to a subject.

The NO-sGC-cGMP Pathway

In the body, nitric oxide (NO) is synthesized from arginine and oxygen by various nitric oxide synthase (NOS) enzymes and by sequential reduction of inorganic nitrate. Three distinct isoforms of NOS have been identified: inducible NOS (iNOS or NOS II) found in activated macrophage cells; constitutive neuronal NOS (nNOS or NOS I), involved in neurotransmission and log-term potentiation; and constitutive endothelial NOS (eNOS or NOS III), which regulates smooth muscle relaxation and blood pressure. Experimental and clinical evidence has indicated that reduced NO concentrations, reduced NO bioavailability and/or reduced responsiveness to endogenously produced NO contributes to the development of disease.

sGC is the primary receptor enzyme for NO in vivo. sGC cap be activated via both NO-dependent and NO-independent mechanisms. In response to this activation, sGC converts guanosine-5'-triphosphate (GTP) into the secondary messenger cyclic guanosine 3', 5'-monophosphate (cGMP). The increased level of cGMP, in turn, modulates the activity of downstream effectors including protein kinases, phosphodiesterases (PDEs) and ion channels.

Two classes of compounds have been identified in the last decades that are able to activate the sGC receptor: sGC stimulators and sGC activators. NO-independent, heme-dependent, sGC stimulators have displayed several important differentiating characteristics when compared with NO-independent, heme-independent sGC activators. These include crucial dependency on the presence of the reduced prosthetic heme moiety for their activity and strong synergistic enzyme activation when combined with NO. The benzylindazole compound YC-1 was the first sGC stimulator to be identified. Additional sGC stimulators with improved potency and specificity for sGC have since been developed.

Increased concentration of cGMP as a result of sGC stimulation leads to vasodilation, inhibition of platelet aggregation and adhesion, anti-hypertensive effects, anti-remodeling effects, anti-apoptotic effects, anti-inflammatory effects, anti-fibrotic effects and neuronal signal transmission effects in animal models. Thus, sGC stimulators may be used to treat and/or prevent a range of diseases and disorders, including kidney disease. sGC stimulators may also be useful in the prevention and/or treatment of diseases and disorders characterized by undesirable reduced bioavailability of and/or sensitivity to NO, such as those associated with conditions of oxidative stress or nitrosative stress. Compounds that stimulate sGC in an NO-independent manner offer considerable advantages over other alternative therapies that either target the aberrant NO pathway or otherwise benefit from the upregulation of the NO pathway, such as inter alia, arginine, NO-donors, or PDES inhibitors.

Praliciguat (IW-1973)

Compound I (pralicguat, prl, IW-1973, IWP-121) is a novel sGC stimulator characterized by multidimensional pharmacology and extensive distribution to multiple tissue beds in animal models, including the renal medulla and cortex (Tobin J V et al. (2018), "Pharmacological Characterization of IW-1973, a Novel Soluble Guanylate Cyclase Stimulator with Extensive Tissue Distribution, Antihypertensive, Anti-Inflammatory, and Antifibrotic Effects in Preclinical Models of Disease", 365, pp. 664-675; Buys E S et al. (2018) "Discovery and development of next generation sGC stimulators with diverse multidimensional pharmacology and broad therapeutic potential", Nitric Oxide, 78, pp. 72-81).

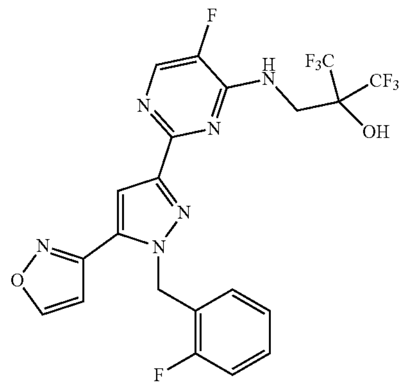 [SMILES: OC(CNc1nc(-c2cc(-c3ccon3)n(Cc3ccccc3F)n2)ncc1F)(C(F)(F)F)C(F)(F)F]

The present invention is based on the surprising finding that an sGC stimulator Compound I administered at specific dosage regimens to a population of DN patients demonstrated the ability to positively affect relevant clinical markers associated with DN.

It is also based on the surprising finding that the sGC stimulator Compound I administered at specific dosage regimens to a population of DN patients improved albuminuria in said patients when compared to placebo. In certain embodiments, the patient has a value of eGFR between 30 and 45 mL/min/1.73 $m^2$. In certain embodiments, the patient has a value of eGFR between 45 and 60 mL/min/1.73 $m^2$.

It is also based on the surprising finding that the sGC stimulator Compound I administered at specific dosage regimens to a sub-population of DN patients with values of eGFR between 30 and 45 mL/min/1.73 $m^2$ had a superior effect on reduction of albuminuria in said patients when compared to placebo.

It is also based on the surprising finding that the sGC stimulator Compound I administered at specific dosage regimens to a population of DN patients improved metabolic parameters in said patients wen compared to placebo.

It is also based on the surprising finding that the sGC stimulator Compound I administered at specific dosage regimens to a population of DN patients reduced blood pressure in said patients when compared to placebo. Even though reductions of blood pressure in diabetic patients has previously been observed by us in human patients, DN patients are known to often be refractory to treatment with other blood pressure medications (Rossignol P, et al. "The double challenge of resistant hypertension and chronic kidney disease." Lancet. 2015 Oct. 17; 386 (10003): 588-98).

Therapeutic Methods

Diagnosis of DN or DKD is based on the presence of albuminuria (urine to albumin creatinine ratio [UACR]>30 mg/g) and/or reduced estimated glomerular filtration rate (eGFR <90 mL/min/1.73 $m^2$) in patients with diabetes. Recent studies and meta-analyses have supported the relationship between reductions in urine albumin loss (as measured by UACR determination) and slowing the decline of renal function for interventions in chronic kidney disease, including DKD (Cherney D Z I et al. "Effects of empagliflozin on the urinary albumin-to-creatinine ratio in patients with type 2 diabetes and established cardiovascular disease: an exploratory analysis from the EMPA-REG OUTCOME randomised, placebo-controlled trial" Lancet Diabetes Endocrinol., 5(8), 610-621, 2017; Coresh J. et al. "Change in albuminuria and subsequent risk of end-stage kidney disease: an individual participant-level consortium meta-analysis of observational studies" Lancet Diabetes Endocrinol., 7(2), 115-127, 2019; Heerspink H J L et al. "Change in albuminuria as a surrogate endpoint for progression of kidney disease: a meta-analysis of treatment effects in randomised clinical trials" Lancet Diabetes Endocrinol., 7(2), 128-139, 2019). Thus, attenuation of albuminuria in early-stage clinical trials could be a predictor of long-term renal benefit in patients with diabetes, including preservation of kidney function and delaying or preventing progression to ESKD or renal replacement therapy (in the form of dialysis or transplant) and progression to death.

The goal of the study described in the Experimental Section was to assess the tolerability and safety of praliciguat in patients with type 2 diabetes mellitus (T2D) and moderate to severe albuminuria that were on stable doses of RAAS inhibitors, and to determine if albuminuria was reduced following 12 weeks of treatment. In some embodiments of the methods and uses of the invention, the patient has a UACR value higher than 200 mg/g and lower than 5000 mg/g at the start of treatment. In other embodiments of the methods and uses of the invention, the patient has a UACR value higher than 200 mg/g at the start of treatment. In some embodiments of the methods and uses of the invention, the patient has a UACR value lower than 5000 mg/g at the start of treatment. In some embodiments of the methods and uses of the invention, the patient has a UACR value between 30 mg/g and 300 mg/g or between 30 mg/g and 200 mg/g. In some embodiments of the methods and uses of the invention, the patient is on a stable regimen of an ACEi or an ARB at the start of treatment.

Estimated glomerular filtration rate (eGFR) is a measure of the level of function of the kidneys. As used herein, eGFR is measured by the Chronic Kidney Disease Epidemiology Collaboration (CKD-EPI) creatinine equation (Levey A S, Stevens L A, Schmid C H, Zhang Y L, Castro A F, Feldman H I, et al. (2009) "A new equation to estimate glomerular filtration rate" *Annals of Internal Medicine,* 150 (9):604-12).

In some embodiments of the methods and uses of the invention, the patient has a eGFR between 30 and 45 mL/min/1.73 $m^2$ at the start of treatment. In other embodiments the patient has a eGFR between higher than 45 and 60 mL/min/1.73 $m^2$ at the start of treatment. In still other embodiments, the patient has a eGFR between higher than 60. and 75 mL/min/1.73 $m^2$ at the start of treatment. In certain embodiments, the patient has a eGFR between 75 and 90 mL/min/1.73 $m^2$ at the start of treatment.

In certain embodiments of the methods and uses of the present invention, the patient has a HOMA-IR level of 2.9 or higher, indicative of significant insulin resistance.

In some embodiments of the above methods and uses, the sGC stimulator is administered before a symptom of a disease, disorder or condition fully develops in said patient. In other embodiments of the above methods and uses, the sGC stimulator is administered after one or more symptoms of a disease, disorder or condition develops in said patient.

A skilled person would be able to use routine means (e.g., including, but not limited to laboratory tests, physical exams, cognitive tests, imaging tools, etc.) to determine improvement in the measurable clinical or pathological parameters or assessments.

In some embodiments of the methods and uses of the present invention, the patient has a history of hypertension. In some of these embodiments, the patient is on at least 1 antihypertensive medication. In other embodiments the patient has seated blood pressure [BP]>140/90 mmHg before the start of treatment. In other embodiments the patient has seated blood pressure [BP]>130/85 mmHg before the start of treatment. In other embodiments, the patient is on a stable regimen of I 6'more antihypertensive medications.

In certain embodiments of the methods and uses of the present invention, the patient has systolic blood pressure ≥140 mm Hg and/or diastolic blood pressure ≥90 mm Hg before the start of treatment. In certain embodiments of the methods and uses of the present invention, the patient has systolic blood pressure ≥130 mm Hg and/or diastolic blood pressure ≥85 mm Hg before the start of treatment.

In certain embodiments of the methods and uses of the present invention, the patient has a fasting blood glucose level of 150 mg/dL or higher. In certain embodiments of the methods and uses of the present invention, the patient has a fasting blood glucose level of 140 mg/dL or higher. In certain embodiments of the methods and uses of the present invention, the patient has a fasting blood glucose level of 130 mg/dL or higher. In certain embodiments of the methods and uses of the present invention, the patient has a fasting blood glucose level of 120 mg/dL or higher. In other embodiments, the patient has a fasting blood glucose level of 110 mg/dL or higher. In other embodiments, the patient has a fasting blood glucose level of 100 mg/dL or higher. In other embodiments, a patient has a fasting blood glucose level of 95 mg/dL or higher. In still other embodiments, the patient has been diagnosed as having type 2 diabetes mellitus. In other embodiments the patient has been diagnosed as having prediabetes. In some of these embodiments, the patient is being treated for diabetes or prediabetes. In yet other embodiments, the patient has a value of hemoglobin A1c≥5.6%. %. In still other embodiments, the patient has a value of hemoglobin A1c≥6.5%. In still other embodiments, the patient has a value of hemoglobin A1c≥7.0%. In still other embodiments, the patient has a value of hemoglobin A1c equal or below 12%. In still other embodiments, the patient has a value of hemoglobin A1c between 7.0 and 8.5%. In still other embodiments, the patient has a value of hemoglobin A1c between 7.5 and 8.5%. In some embodiments, the patient is on a stable regimen of 1 or more antihyperglycemic medications.

In certain embodiment of the methods and uses of the present invention, the patient has a waist circumference of 102 cm (40 inches) or more for men and 88 cm (35 inches) or more for women.

In some embodiments of the methods and uses of the present invention, the patient has a body mass index (BMI)

>25 kg/$m^2$. In other embodiments, the patient has a BMI higher than 30 kg/$m^2$. In still other embodiments the BMI is higher than 40 kg/m.

In some embodiments of the methods and uses of the present invention, the patient has fatty liver disease. In some embodiments the patient has non alcoholic fatty liver disease (NAFLD). In other embodiments, the patient has NASH.

In certain embodiments, for the methods and uses of the present invention described herein, the human patient has DN. In some embodiments, the human patient is an adult. In other embodiments, the human patient is between 50 and 75 years old. In other embodiments, the patient is between 55 and 70 years old.

In some embodiments of the methods and uses of the present invention the patient is an African-American, Native American or Asian-American. In some embodiments the patient is an African-American. In other embodiments, the patient is a Native American. In still other embodiments, the patient is an Asian-American. In yet further embodiments, the patient is Asian. In yet other embodiments, the patient is African. In yet other embodiments, the patient is black. In still other embodiments, the patient is white. In yet other embodiments, the patient is latino. In still other embodiments, the patient is non-lation.

In certain embodiments, the methods and uses of the present invention described herein comprise administering to the patient a single oral daily dose of between 10 mg and 40 mg, between 10 mg and 20 mg, between 20 mg and 40 mg, between 20 mg and 30 mg or between 30 mg and 40 mg of Compound I.

In certain embodiments, the methods and uses of the present invention described herein comprise administering to the patient a single oral daily dose of 10 mg of Compound I.

In certain embodiments, the methods and uses of the present invention described herein comprise administering to the patient a single oral daily dose of 15 mg of Compound I.

In certain embodiments, the methods and uses of the present invention described herein comprise administering to the patient a single oral daily dose of 20 mg of Compound I.

In certain embodiments, the methods and uses of the present invention described herein comprise administering to the patient a single oral daily dose of 25 mg of Compound I.

In certain embodiments, the methods and uses of the present invention described herein comprise administering to the patient a single oral daily dose of 30 mg of Compound I.

In certain embodiments, the methods and uses of the present invention described herein comprise administering to the patient a single oral daily dose of 40 mg of Compound I.

In certain embodiments, the methods and uses of the present invention described herein comprise administering to the patient an oral dose of 5 mg of Compound I twice a day. In one embodiment, the methods and uses comprise administering to the patient a first oral dose of 5 mg and a second oral dose of 5 mg, wherein the first dose and the second dose are separated by a period between 5 hours and 15 hours, between 8 hours and 15 hours, or between 10 hour and 15 hours. In another embodiment, the first dose and the second dose are separated by 5 hours, 6 hours, 7 hours, 8 hours, 9 hours, 10 hours, 11 hours, 12 hours, 13 hours, 14 hours, or 15 hours.

In certain embodiments, the methods and uses of the present invention described herein comprise administering to the patient an oral dose of 7.5 mg of Compound I twice a day. In one embodiment, the method and uses comprise administering to the patient a first oral dose of 7.5 mg and a second oral dose of 7.5 mg, wherein the first dose and the second dose are separated by a period between 5 hours and 15 hours, between 8 hours and 15 hours, or between 10 hour and 15 hours. In another embodiment, the first dose and the second dose are separated by 5 hours, 6 hours, 7 hours, 8 hours, 9 hours, 10 hours, 11 hours, 12 hours, 13 hours, 14 hours, or 15 hours.

In certain embodiments, the methods and uses of the present invention described herein comprise administering to the patient an oral dose of 10 mg of Compound I twice a day. In one embodiment, the method and uses comprise administering to the patient a first oral dose of 10 mg and a second oral dose of 10 mg, wherein the first dose and the second dose are separated by a period between 5 hours and 15 hours, between 8 hours and 15 hours, or between 10 hour and 15 hours. In another embodiment, the first dose and the second dose are separated by 5 hours, 6 hours, 7 hours, 8 hours, 9 hours, 10 hours, 11 hours, 12 hours, 13 hours, 14 hours, or 15 hours.

In certain embodiments, the methods and uses of the present invention described herein comprise administering to the patient an oral dose of 12.5 mg of Compound I twice a day. In one embodiment, the method and uses comprise administering to the patient a first oral dose of 12.5 mg and a second oral dose of 12.5 mg, wherein the first dose and the second dose are separated by a period between 5 hours and 15 hours, between 8 hours and 15 hours, or between 10 hour and 15 hours. In another embodiment, the first dose and the second dose are separated by 5 hours, 6 hours, 7 hours, 8 hours, 9 hours, 10 hours, 11 hours, 12 hours, 13 hours, 14 hours, or 15 hours.

In certain embodiments, the methods and uses of the present invention described herein comprise administering to the patient an oral dose of 20 mg of Compound I twice a day. In one embodiment, the methods-arid uses comprise administering to the patient a first oral dose of 20 mg and a second oral dose of 20 mg, wherein the first dose and the second dose are separated by a period between 5 hours and 15 hours, between 8 hours and 15 hours, or between 10 hour and 15 hours. In another embodiment, the first dose and the second dose are separated by 5 hours, 6 hours, 7 hours, 8 hours, 9 hours, 10 hours, 11 hours, 12 hours, 13 hours, 14 hours, or 15 hours.

In certain embodiments, the methods and uses of the present invention described herein comprise administering to the patient an oral dose of 15 mg of Compound I twice a day. In one embodiment, the methods the uses comprise administering to the patient a first oral dose of 15 mg and a second oral dose of 15 mg, wherein the first dose and the second dose are separated by a period between 5 hours and 15 hours, between 8 hours and 15 hours, or between 10 hour and 15 hours. In another embodiment, the first dose and the second dose are separated by 5 hours, 6 hours, 7 hours, 8 hours, 9 hours, 10 hours, 11 hours, 12 hours, 13 hours, 14 hours, or 15 hours.

In some embodiments, the methods and uses of the present invention described herein comprise the administration of an initial dose of between 10 mg and 20 mg once a day to the patient for a period between 0.7 and 14 days, followed by an increase to a maintenance dose of between 20 mg and 40 mg once a day.

In some embodiments, the maintenance dose continues indefinitely as long as the patient continues to experience clinical benefit. Accordingly, in some embodiments, the methods and uses of the present invention described herein comprise administering to the patient an initial oral dose of between 10 mg and 20 mg once per day for a period of between 7 days and 14 days; and subsequently administering to the patient a maintenance dose of between 20 mg and 40 mg once per day. In some embodiments, the administration of the maintenance dose continues indefinitely as long as the patient continues to experience clinical benefit with minimal undesired side effects.

In some embodiments, the methods and uses of the present invention described herein comprise the administration of an initial dose of between 5 mg and 20 mg twice a day to the patient for a period between 7 and 14 days, followed by a maintenance dose of between 10 mg and 40 mg once a day. In some embodiments, the methods and uses of the present invention described herein comprise the administration of an initial dose of 5 mg twice a day to the patient for a period between 7 and 14 days, followed by a maintenance dose of 10 mg once a day, In some embodiments, the methods and uses of the present invention described herein comprise the administration of an initial dose of 7.5 mg twice a day to the patient for a period between 7 and 14 days, followed by a maintenance dose of 15 mg once a day. In some embodiments, the methods and uses of the present invention described herein comprise the administration of an initial dose of 10 mg twice a day to the patient for a period between 7 and 14 days, followed by a maintenance dose of 20 mg once a day. In some embodiments, the methods and uses of the present invention described herein comprise the administration of an initial dose of 15 mg twice a day to the patient for a period between 7 and 14 days, followed by a maintenance dose of 30 mg once a day. In some embodiments, the methods and uses of the present invention described herein comprise the administration of an initial dose of 20 mg twice a day to the patient for a period between 7 and 14 days, followed by a maintenance dose of 40 mg once a day. In some embodiments, the administration of the maintenance dose continues indefinitely as long as the patient continues to experience clinical benefit with minimal undesired side effects.

In some embodiments, the methods and uses of the present invention described herein comprise the administration of an initial total oral daily dose of 10 mg for a period between 3 and 14 days, followed by a total oral daily dose of 20 mg for a period between 3 and 14 days and then followed by an increase to a maintenance dose of 40 mg. In some embodiments, step-ups to 15 mg or 25 mg, between 3 and 14 days each can be added. In some embodiments, the methods and uses of the present invention described herein comprise the administration of an initial total oral daily dose of 10 mg for a period between 3 and 14 days, followed by a total oral daily dose of 15 mg for a period between 3 and 14 days, followed by a total oral daily dose of 20 mg for a period between 3 and 14 days and then followed by an increase to a maintenance dose of 40 mg. In some embodiments, the methods and uses of the present invention described herein comprise the administration of an initial total oral daily dose of 10 mg for a period between 3 and 14 days, followed by a total oral daily dose of 15 mg for a period between 3 and 14 days, followed by a total oral daily dose of 20 mg for a period between 3 and 14 days, followed by a total oral daily dose of 25 mg for a period between 3 and 14 days and then followed by an increase to a maintenance dose of 40 mg. In some embodiments, the administration of the maintenance dose continues indefinitely as long as the patient continues to experience clinical benefit with minimal undesired side effects. In some embodiments, the methods and uses of the present invention described herein comprise the administration of an initial total oral daily dose of 10 mg for a period between 3 and 14 days, followed by a total oral daily dose of 15 mg for a period between 3 and 14 days, followed by a maintenance total oral daily dose of 20 mg. In some embodiments, the methods and uses of the present invention described herein comprise the administration of an initial total oral daily dose of 10 mg for a period between 3 and 14 days, followed by a total oral daily dose of 15 mg for a period between 3 and 14 days, followed by a total oral daily dose of 20 mg, followed by a total maintenance total oral dose of 30 mg.

In other embodiments, the methods and uses of the present invention described herein comprise the administration of an initial oral daily dose of between 15 mg and 40 mg once a day to the patient, followed by a decrease to a maintenance daily dose of between 7.5 mg and 20 mg once a day if the patient experiences hypotension. In some embodiments, the maintenance dose continues indefinitely as long as the patient continues to experience clinical benefit with minimal undesired hypotensive effects. Accordingly, in some embodiments, the methods and uses of the present invention described herein comprise administering to the patient an initial oral daily dose of between 15 mg and 40 mg once per day; and subsequently administering to the patient a maintenance dose of between 7.5 mg and 20 mg once per day if the patient experiences hypotension. In some embodiments, the administration of the maintenance dose continues indefinitely as long as the patient continues to experience clinical benefit with minimal undesired hypotensive effects.

In some embodiments, if the patient is taking a strong CYP3A inhibitor concomitantly with Compound I, the observed AUC and $T_{1/2}$ for Compound I is doubled as compared to the AUC and $T_{1/2}$ observed for a patient that is not concomitantly taking a strong CYP3A inhibitor (see trial no. NCT03499106 at https//clinicaltrials.gov). For these embodiments, the methods and uses of the present invention described herein comprise the use of half a dose of Compound I to achieve the same results that a full dose would achieve in a patient not concomitantly taking a strong CYP3A inhibitor.

Examples of strong CYP3A inhibitor include, but are not limited to, azole antifungals, macrolide antibiotics, protease inhibitors, and diltiazem.

In certain embodiments, the methods and uses of the present invention described herein further comprise administering to the patient one or more (two, three, four, five, etc.) anti-hypertensive medications. In one embodiment, the one or more anti-hypertensive medications are each independently selected from an angiotensin-converting enzyme (ACE) inhibitor, an angiotensin II receptor blocker (ARB), a MR antagonist (MRA), an endothelin receptor antagonist (ERA) and a diuretic. In certain embodiments, the one or more anti-hypertensive medications are each independently selected from an angiotensin-converting enzyme (ACE) inhibitor, an angiotensin II receptor blocker (ARB), a diuretic, a calcium channel blocker, a beta blocker, a vasodilator, a cetral-acting agent and an aldosterone antagonist. In one embodiment, at least one of the anti-hypertensive medication is an ARB or an ACE inhibitor.

In certain embodiments, the methods and uses of the present invention described herein further comprise administering to the patient one or more (two, three, four, five, etc.) anti-hypertensive medications. In one embodiment, the one or more anti-hypertensive medications are each independently selected from an angiotensin-converting enzyme (ACE) inhibitor and an angiotensin II receptor blocker (ARB). In another embodiment, the one or more anti-hypertensive meditation is independently selected from the group consisting of lisinopril, combinations of lisinopril with hydrochlorothiazide, benazepril, captopril, enalapril, candesartan, losartan, azilsartan, eprosartan, irbesartan, olmesartan, telmisartan and valsartan. In another embodiment, the one or more anti-hypertensive medications are each independently selected from the group consisting of lisinopril, combination of lisinopril and hydrochlorothiazide, enalapril, losartan, metoprolol, and spironolactone. In another embodiment, the one or more anti-hypertensive medications are each independently selected from the group consisting of lisinopril, combination of lisinopril and hydrochlorothiazide, enalapril, and losartan. In one embodiment, at least one of the anti-hypertensive medication is an angiotensin-converting enzyme (ACE) inhibitor or an angiotensin II receptor blocker (ARB). In another embodiment, at least one of the anti-hypertensive medication is selected from the group consisting of lisinopril, combination of lisinopril and hydrochlorothiazide, enalapril, and losartan.

In certain embodiments, the methods and uses of the present invention described herein further comprise administering to the patient two or more (three, four, five, etc.) anti-hypertensive medications. In certain embodiments, at least one of the anti-hypertensive medication is an angiotensin-converting enzyme (ACE) inhibitor or an angiotensin II receptor blocker (ARB) and at least one of the anti-hypertensive medication is a diuretic. In certain embodiments, the diuretic is selected from chlorthalidone and hydrochlorothiazide.

In certain embodiments, the methods and uses of the present invention described herein further comprise administering to the patient three or more (four, five, six etc.) anti-hypertensive medications. In certain embodiments, at least one of the anti-hypertensive medication is an angiotensin-converting enzyme (ACE) inhibitor or an angiotensin II receptor blocker (ARB); at least one of the anti-hypertensive medication is a diuretic; and at least one of the anti-hypertensive medication is selected from a calcium channel blocker and a beta blocker. In certain embodiments, the diuretic is selected from chlorthalidone and hydrochlorothiazide.

In certain embodiments, the methods and uses of the present invention described herein further comprise administering to the patient four or more (five, six etc.) anti-hypertensive medications. In certain embodiments, at least one of the anti-hypertensive medication is an angiotensin-converting enzyme (ACE) inhibitor or an angiotensin II receptor blocker (ARB); at least one of the anti-hypertensive medication is a diuretic; at least one of the anti-hypertensive medication is selected from a calcium channel blocker and a beta blocker; and at least one of the anti-hypertensive medication is selected from a vasodilator, a central-acting agent and an aldosterone antagonist. In certain embodiments, the diuretic is selected from chlorthalidone and hydrochlorothiazide. In certain embodiment, the vasodilator is selected from hydralazine and minoxidil. In certain embodiments, the central-acting agent is clonidine. In certain embodiments, the aldosterone antagonist is selected from spironolactone and eplerenone.

In certain embodiments, the methods and uses of the present invention described herein further comprise administering to the patient one or more (two, three, four, five, etc.) blood glucose lowering medication's (anti hyperglycemic or antidiabetes drugs). In one embodiment, the one or more blood glucose lowering medications are independently selected from the group consisting of insulin, metformin, glyburide, glipizide, glimepiride, repaglinide, nateglinide, sitagliptin, saxagliptin, linagliptin, exenatide, liraglutide, semaglutide, canagliflozin, and dapagliflozin. In certain embodiment, insulin is not given or administered to the patient treated with the methods described herein during the treatment with Compound I. In some embodiments, the patient is being treated with an oral antihyperglycemic agent in addition to Compound I.

In certain embodiments, the methods and uses of the present invention described herein further comprise administering to the patient an anti-hypertensive medication described herein and a blood glucose lowering medication described herein. In one embodiment, the methods and uses further comprise administering to the patient one or more anti-hypertensive medications independently selected from the group consisting of isinopril, combination of lisinopril and hydrochlorothiazide, enalapril, losartan, metoprolol, and spironolactone and one or more blood glucose lowering medications independently selected from the group consisting of insulin, metformin, and glipizide. In one embodiment, at least one of the anti-hypertensive medication is an angiotensin-converting enzyme (ACE) inhibitor or an angiotensin II receptor blocker (ARB). In another embodiment, at least one of the anti-hypertensive medication is selected from the group consisting of lisinopril, combination of lisinopril and hydrochlorothiazide, enalapril, and losartan.

In certain embodiments, the methods of the present invention described herein further comprise administering to the patient one or more (two, three, four, five, etc.) anti-hyperlipidemic medications. In one embodiment, the one or more anti-hyperlipidemic medications is selected from a cholesterol lowering medication. In one embodiment, the one or more anti-hyperlipidemic medications are independently selected from the group consisting of atorvastin, pravastatin, simvastatin, rosuvastatin, lovastatin and nicotinic acid. In another embodiment, the one or more cholesterol lowering medication is selected from the group consisting of atorvastin, pravastatin, rosuvastatin, lovastatin and simvastatin.

In certain embodiments, the methods and uses of the present invention described herein further comprise administering to the patient one or more (two, three, four, five, etc.) neprilysin inhibitors. In one embodiment, the neprilysin inhibitor is sacubitril or the combination of sacubitril and valsartan.

In certain embodiments, the methods and uses of the present invention described herein are indicated for the improvement in albuminuria in the patient. In some embodiments, the improvement in albuminuria is measured by a decrease in UACR of the patient. In certain embodiments, the methods and uses of the present invention described herein result in a decrease in UACR between 10% and 40%, between 20% and 40%, between 20% and 30% or between 30% and 40%. In certain embodiments, the patient has a value of eGFR between 30 and 45 mL/min/1.73 $m^2$ and the methods and uses of the present invention described herein result in a decrease in UACR between 10% and 40%, between 20% and 40%, between 20% and 30% or between 30% and 40%.

In certain embodiments, the methods and uses of the present invention described herein are indicated to delay or prevent the clinical worsening in the patient. In some embodiments, the methods and uses of the present invention described herein are indicated for the delay or prevention in the progression to ESKD or a delay or prevention in the need of renal replacement therapy (dialysis or kidney transplant). In other embodiments, the methods and uses of the present invention described herein result in a reduction in hospitalizations for a renal cause. In some embodiments the renal cause is uremia. In other embodiments, the methods and uses of the present invention described herein result in delay or prevention of the worsening of renal function. In certain embodiments, the worsening of renal function is defined by doubling of serum creatinine values. In certain embodiments, the worsening of renal function is defined as 40% or greater decline in eGFR in a period of time of 1 to 4 years. In some embodiments the period is one year (fast worsening). In other embodiments the period of worsening is 2 years. In other embodiments the period of worsening is 3 years. In other embodiments, the period of worsening is 4 years (slow worsening).

In certain embodiments, the methods and uses of the present invention described herein result in an increase in the survival of the patient. In other embodiments they result in a delay in time to death.

In certain embodiments, the methods and uses of the present invention described herein are indicated for the lowering blood pressure (BP) in the patient with diabetes. In certain embodiments, the methods and uses of the present invention described herein results in a reduction in MAP of the patient. In certain embodiment, the reduction in MAP is in the range of 1 mmHg and 10 mmHg, 1 mmHg and 6 mmHg, 2 mmHg and 6 mmHg, or 3 mmHg and 4 mmHg. In certain embodiments, the methods and uses of the present invention described herein results in a reduction in systolic blood pressure of the patient. In certain embodiments, the reduction in systolic blood pressure is in the range of 1 mmHg and 10 mmHg, 1 mmHg and 8 mmHg, 4 mmHg and 6 mmHg, or 4 mmHg and 5 mmHg. In certain embodiments, the BP measurement is seated-BP measurement. In one embodiment, the BP measurement is seated-BP measure with automated office equipment. In other embodiments, the BP measurement is the average 24-hour BP measurement with ambulatory monitoring equipment. In certain embodiments, the BP measurement is for systolic blood pressure, diastolic blood pressure and/or MAP. In certain embodiments, the methods and uses of the present invention described herein result in a reduction in seated-BP (e.g., systolic blood pressure, diastolic blood pressure and/or MAP) of the patient. In certain embodiments, the reduction in seated-BP (e.g., systolic blood pressure, diastolic blood pressure and/or MAP) is in the range of 1 mmHg and 10 mmHg, 1 mmHg and 8 mmHg, 1 mmHg and 6 mmHg, 2 mmHg and 6 mmHg, 4 mmHg and 6 mmHg, 4 mmHg and 5 mmHg, or 3 mmHg and 4 mmHg. In certain embodiments, the methods and uses of the present invention described herein decrease UACR of the patient as described above and, at least part of the decrease in UACR observed is independent of the change in blood pressure of the patient. In certain embodiments, the decrease in UACR is not associated with a significant reduction in MAP of the patient. In certain embodiments, the decrease in UACR is not associated with a significant reduction in diastolic blood pressure of the patient. In certain embodiments, the decrease in UACR is not associated with a significant reduction in systolic blood pressure of the patient. In certain embodiments, the decrease in UACR is not associated with a significant reduction in seated-BP (e.g., systolic blood pressure, diastolic blood pressure and/or MAP) of the patient. As used herein, a "significant" reduction refers to a reduction in blood pressure that is more than 5 mm Hg, more than 4 mm Hg, more than 3 mm Hg, more than 2 mm Hg, or more than 1 mm Hg.

In certain embodiments, the methods and uses of the present invention described herein result are indicated for the improvement in metabolic outcomes in the patient, including the reduction in the risk for CV events. The potential for certain metabolic outcomes in a patient is known to be related to high elevated values of various metabolic parameters, such as fasting plasma glucose, hemoglobin A1c (HbA1C), fasting plasma insulin, HOMA-IR, serum total cholesterol, LDL cholesterol and triglycerides. In some embodiments, the methods and uses of the present invention result in reductions in one or more metabolic parameters. In some embodiments the reductions are in one or more parameters selected from fasting plasma glucose, HbA1C, serum total cholesterol and serum LDL-cholesterol. In certain embodiments, the reduction in fasting plasma glucose of the patient is in the range of 1% and 30%, 1% and 20%, 1% and 10%, or 1% and 5%. In certain embodiments the reduction in HbA1C is in the range of 0.1% and 1%, 0.1% and 0.6%, 0.2% and 0.4% or 0.3% and 0.4%. In certain embodiments, the reduction in serum total cholesterol is in the range of 1 mg/dL and 30 mg/dL, 1 mg/dL and 20 mg/dL, 1 mg/dL and 10 mg/dL, 1 mg/dL and 8 mg/dL, 3 mg/dL and 8 mg/dL, or 4 mg/dL and 6 mg/dL. In certain embodiments, the reduction in serum LDL cholesterol is in the range of 1 mg/dL and 30, 1 mg/dL and 20 mg/dL, 1 mg/dL and 10 mg/dL, 1 mg/dL and 8 mg/dL, 3 mg/dL and 7 mg/dL, or 3 mg/dL and 6 mg/dL.

In some embodiments, the methods and uses of the present invention described herein are indicated for the reduction of CV event risk. In certain embodiments, the methods and uses of the present invention described herein result in an improvement of metabolic outcomes in the patient.

In certain embodiments, the improvements in albuminuria (e.g., decrease in UACR), the delay or prevention in clinical worsening, the lowering of blood pressure (e.g., reducting in MAP, reduction in systolic blood pressure, reduction in seated-BP), and/or the improvement in metabolic outcomes (e.g., reduction in the risk for CV events, reduction in fasting plasma glucose, hemoglobin A1c (HbA1C), fasting plasma insulin, HOMA-IR, serum total cholesterol, LDL-cholesterol and/or triglycerides), in the patient is observed after the patient has been treated with the methods for a period of time. In certain embodiments, the improvements in albuminuria (e.g., decrease in UACR), the delay or prevention in clinical worsening, the lowering of blood pressure (e.g., reducting in MAP, reduction in systolic blood pressure, reduction in seated-BP), and/or the improvement in metabolic outcomes (e.g., reduction in the risk for CV events, reduction in fasting plasma glucose, hemoglobin A1c (HbA1C), fasting plasma insulin, HOMA-IR, serum total cholesterol, LDL-cholesterol and/or triglycerides), in the patient is observed after 4 weeks, after 6 weeks, after 8 weeks, after 10 weeks, after 12 weeks, after 16 weeks, after 20 weeks, after 6 months, after 8 months, after 12 months or after 24 months of the treatment.

Combination Therapies

The treatment of DN and related symptoms with Compound I can be carried out using the compound alone or in combination therapy with other therapeutic agents. In some particular embodiments, Compound I can be used for the treatment of DN in combination with one or more medications independently selected from antihypertensive medications, blood glucose reducing medications, antihyperlipidemics, renoprotective medications and neprilysin inhibitors.

The sGC stimulator Compound I can be used in combination therapy with one or more additional therapeutic agents (e.g, additional therapeutic agents described herein). For combination treatment with more than one therapeutic agents, where the therapeutic agents are in separate dosage formulations, or dosage forms, the therapeutic agents may be administered separately or in conjunction (i.e., at the same time). In addition, when administered separately, the administration of one therapeutic agent may be prior to or subsequent to the administration of the other agent.

When Compound I is used in combination therapy with other therapeutic agents, a therapeutically effective amount of the other therapeutic agent or each of the other therapeutic agents will depend on the type of drug used. Suitable dosages are known for approved therapeutic agents and can be adjusted by the skilled artisan according to the condition of the subject, the type of condition(s) being treated and the amount of a Compound I being used. In one embodiment of this invention, Compound I, and the additional therapeutic agent are each administered in an therapeutically effective amount (i.e., each in an amount which would be therapeutically effective if administered alone). In other embodiments, Compound I and the additional therapeutic agent are each administered in an amount which alone does not provide a therapeutic effect (a sub-therapeutic dose). In yet another embodiment, Compound I can be administered in an effective therapeutic amount, while the additional therapeutic agent is administered in a sub-therapeutic dose. In still another embodiment, Compound I can be administered in a sub-therapeutic dose, while the additional therapeutic agent is administered in a therapeutically effective amount.

When co-administration involves the separate administration of a first amount of Compound I and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and pharmacokinetic profile. For example, Compound I and the second therapeutic agent can be administered in any order within 24 hours of each other, within 16 hours of each other, within 8 hours of each other, within 4 hours of each other, within 1 hour of each other, within 30 minutes of each other, within 5 minutes of each other, simultaneously or concomitantly.

More, specifically, a first therapy can be administered prior to (e.g., 5 minutes, 15 minutes, 30 minutes, 45 minutes, 1 hour, 2 hours, 4 hours, 6 hours or 12 hours before)), concomitantly with, or subsequent to (e.g., 5 minutes, 15 minutes, 30 minutes, 45 minutes, 1 hour, 2 hours, 4 hours, 6 hours, 12 hours after), the administration of a second therapy to a subject.

Examples of other therapeutic agents that may be combined with Compound I include, but are not limited to those discussed below.

1. Blood glucose lowering medications (also referred as glycemic control medications or antidiabetic medications) that may be used in combination with Compound I include, but are not limited to:

Biguanides.

Generally, the biguanide metformin is the first medication prescribed for type 2 diabetes. It works by improving the sensitivity of body tissues to insulin so that the body uses insulin more effectively. Metformin also lowers glucose production in the liver. Metformin may not lower blood sugar enough on its own. If metformin and lifestyles changes are not enough to control blood sugar levels, other oral or injected medications can be added, such as the types below.

Sulfonylureas.

Examples of medications in this class include glyburide, glybenclamide, glipizide, gliclazide, gliquidone, glimepiride, atorvastatin calcium combined with glimerpiride, meglinatide, tolbutamide, chlorpropamide, acetohexamide, and tolazimide. In certain embodiment, the sulfonylurea that can be used in combination with Compound I in the treatment of DN is selected from glyburide, glipizide and glimepiride.

Alpha-Glucosidase Inhibitors.

For example, acarbose, epalrestat, voglibose, and miglitol.

Insulin Secretagoges.

Examples include repaglinide, mitiglinide and nateglinide. In certain embodiments, the insulin secretagoge that can be used in combination with Compound I in the treatment of DN is repaglinide or nateglinide.

Thiazolidinediones.

For example, rosiglitazone, troglitazone, ciglitazone, pioglitazone, englitazone, lobeglitazone sulfate and balaglitazone.

DPP-4 Inhibitors (or DPP-IV Inhibitors).

Examples of these medications are sitagliptin, vildagliptin, saxagliptin, alogliptin, linagliptin, alogliptin benzoate combined with metformin or metformin hydrochloride, anagliptin, teneligliptin, atorvastatin calcium and glimepiride, empagliflozin combined with linagliptin, gemigliptin, sitagliptin phosphate monohydrate combined with pioglitazone hydrochloride, sitagliptin combined with pioglitazone, sitagliptin combined with atorvastatin calcium, and (2S,4S)-1-[2-(1,1-dimethyl-3-oxo-3-pyrrolidin-1-yl-propylamino) acetyl]-4-fluoro-pyrrolidine-2-carbonitrile (DBPR-108). "In certain embodiments, the DDP-4 inhibitor that can be used in combination with Compound I in the treatment of DN is sitagliptin, saxagliptin or linagliptin.

GLP-1 Receptor Agonists or Incretin Mimetics.

Examples include exenatide, dulaglutide, liraglutide, semaglutide, lixisenatide, lixisenatide combined with insulin glargine, albiglutide and pegapamodutide (TT-401), LY3298176 (dual glucose-dependent insulinotropic polypeptide (GIP) and GLP-1 receptor agonist). In certain embodiments, the GLP-1 receptor agonist that can be used in combination with Compound I in the treatment of DN is exenatide, semaglutide or liraglutide. In certain embodiments, the GLP-1 receptor agonist is semaglutide. In certain embodiments, the GLP-1 receptor agonist is oral semaglutide.

SGLT2 Inhibitors (SGLT2is).

Examples include empagliflozin, empaglifozin combined with linagliptin empagliflozin combined with metformin, ipragliflozin, ipragliflozin L-proline, tofogliflozin, sergliflozin etabonate, remogliflozin etabonate, ertugliflozin, ertugliflozin combined with sitagliptin, ertugliflozin combined with metformin, sotagliflozin, canagliflozin, canagliflozin combined with metformin or metformin hydrochloride, dapagliflozin, dapagliflozin combined with metformin or metformin hydrochloride and luseoglifozin, dapagliflozin combined with saxagliptin. In one embodiment, the SGLT2 inhibitor is empagliflozin, canagliflozin or dapagliflozin or combination drugs containing these agents. In another embodiment, the SGLT2 inhibitor is dapagliflozin. In another embodiment, the SGLT2 inhibitor is empagliflozin. In another embodiment, the SGLT2 inhibitor is canagliflozin. In certain embodiments, SGLT2 inhibitor is canagliflozin or dapagliflozin.

SGLT1 Inhibitors or Combinations of SGLT1 and SGLT2 Inhibitors.

Examples include sotagliflozin.

Insulin Therapy.

There are many types of insulin, and they each work in a different way. Options include insulin glulisine, insulin degludec, insulin lispro, insulin aspart, insulin glargine, insulin detemir, insulin isophane, insulin mixtard (human insulin containing both fast-acting (soluble) and long-acting (isophane) insulin, insulin degludec combined with insulin aspart, insulin human (rDNA origin) inhalation powder, recombinant human insulin, hepatic-directed vesicle insulin, insulin tregopi (IN-105), insulin degludec combined with liraglutide, insulin peglispro (LY-2605541) and nodlin.

Tolimidone (a Lyn Kinase Activator).

2. Blood pressure lowering medications (also known as anti-hypertensive medications) that may be used in combination with Compound I include, but are not limited to:

Diuretics.

Diuretics, sometimes called water pills, are medications that act on the kidneys to help the body eliminate sodium and water, reducing blood volume. Diuretics or calcium channel blockers may work better for black and older people than do angiotensin-converting enzyme (ACE) inhibitors alone. Thiazide diuretics are often the first, but not the only, choice in high blood pressure medications. Diuretics include, for example, chlorothiazide, chlorthalidone, hydrochlorothiazide, bendroflumethiazide, cyclopenthiazide, methyclothiazide, polythiazide, quinethazone, xipamide, metolazone, indapamide, cicletanine, furosemide, toresamide, amiloride, spironolactone, canrenoate potassium, eplerenone, triamterene, acetazolamid and carperitide. In certain embodiments, the diuretic that can be used in combination with Compound I in the treatment of DN is spironolactone.

Beta Blockers.

These medications reduce the workload on the heart and open blood vessels, causing the heart to beat slower and with less force. When prescribed alone, beta blockers don't work as well, especially in black and older people, but may be effective when combined with other blood pressure lowering medications. Beta blockers include, for example, acebutolol, atenolol, metoprolol, and nebivolol. In certain embodiments, the beta blockers that can be used in combination with Compound I in the treatment of DN is metoprolol.

Angiotensin-Converting Enzyme (ACE) Inhibitors.

These medications help relax blood vessels by blocking the formation of a natural chemical that narrows blood vessels. ACE inhibitors that may be combined with Compound I in the treatment of DN include, for example, sulfhydryl-containing agents (for example, captopril, zofenopril), dicarboxylate-containing agents (for example, enalapril, quinapril, ramipril, perindopril, lisinopropil, and benazepril); phosphonate-containing agents (for example fosinopril), naturally occurring ACE inhibitors (for example, casokinins, lactokinins, lactotripeptides Val-Pro-Pro and Ile-Pro-Pro), alacepril, delapril, cilazapril, imidapril, temocapril, moexipril, lisinopril, combinations of lisinopril with hydrochlorothiazide, trandolapril and spirapril. In certain embodiments, the ACE inhibitor that can be used in combination with Compound I in the treatment of DN is selected from lisinopril, combinations of lisinopril with hydrochlorothiazide, benazepril, captopril, and enalapril.

Angiotensin II Receptor Blockers (ARBs).

These medications help relax blood vessels by blocking the action, not the formation, of a natural chemical that narrows blood vessels. ARBs include candesartan, losartan, losartan potassium-hydrochlorothiazide, valsartan, candesartan cilexetil, eprosaran, irbesartan, telmisartan, olmesartan medoxomil (or olmesartan), azilsartan medoxomil, azilsartan, amlodipine besylate combined with irbesartan, azilsartan combined with amlodipine besilate, cilnidipine combined with valsartan, fimasartan, irbesartan combined with atorvastatin, irbesartan combined with trichlormethiazide, losartan potassium combined with hydrochlorothiazide and/or amlodipine besylate, pratosartan, atorvastatin calcium combined with losartan potassium, nifedipine and candesartan cilexetil, sacubitril combined with valsartan or LCZ-696, angiotensin AT2 antagonist and TAK-591, and olmesartan medoxomil. In certain embodiments, the ARB that can be used in combination with Compound I in the treatment of DN is selected from candesartan, losartan, eprosaran, irbesartan, olmesartan, telmisartan and valsartan.

Endothelin Receptor Antagonists (ERAs).

For example, atrasentan, bosentan, sitaxentan, ambrisentan, actelion-1 (macitentan), Cyclo (D-trp-D-asp-L-pro-D-val-L-leu) (BQ-123), sparsentan and tezosentan disodium. In some embodiments, the ERA is bosentan.

Mineralocorticoid receptor antagonists (MRAs).

For example, spironolactone, amiloride hydrochloride combined with spironolactone, apararenone or MT-3995, eplerenone, and finerenone (BAY-94-8862). In some embodiments, the MRA is finerenone.

Calcium Channel Blockers.

These medications help relax the muscles of the blood vessels. Calcium channel blockers may work better for black and older people than do ACE inhibitors alone. Some slow heart rate. Calcium channel blockers that can be combined with Compound I for the treatment of DN include, for example, amlodipine, aranidipine, azelnidipine, barnidipine, benidipine, cilnidipine, clevidipine, diltiazem, efonidipine, felodipine, lacidipine, lercanidipine, manidipine, nicardipine, nifedipine, nilvadipine, nimodipine, nisoldipine, nitrendipine, pranidipine, isradipine, verapamil, gallopamil, diltiazem, mibefradil, bepridil, fluspirilene, and fendiline.

Renin Inhibitors.

Aliskiren slows down the production of renin, an enzyme produced by your kidneys that starts a chain of chemical steps that increases blood pressure. It works by reducing the ability of renin to begin this process. Due to a risk of serious complications, including stroke, aliskiren cannot be taken without an ACE inhibitor or an ARB.

Alpha Blockers.

These medications reduce nerve impulses to blood vessels, reducing the effects of natural chemicals that narrow blood vessels. Alpha blockers include doxazosin, prazosin and others.

Alpha-Beta Blockers.

In addition to reducing nerve impulses to blood vessels, alpha-beta blockers slow the heartbeat to reduce the amount of blood that must be pumped through the vessels. Alpha-beta blockers include carvedilol and labetalol.

Central-Acting Agents.

These medications prevent the brain from signaling the nervous system to increase the heart rate and narrow blood vessels. Examples include clonidine, guanfacine and methyldopa.

Vasodilators.

These medications, work directly on the muscles in the walls of the arteries, preventing the muscles from tightening and the arteries from narrowing. Examples of vasodilators include NO-donors such nitroglycerine and hydralazine and minoxidil.

Aldosterone Antagonists.

These drugs block the effect of a natural chemical that can lead to salt and fluid retention, which can contribute to high blood pressure. Examples are finerenone, spironolactone and eplerenone 3. Anti-hyperlipidemic medications that may be used in combination with Compound I include, but are not limited to:

Statins.

Examples of statins include, but are not limited to, atorvastatin fluvastatin, lovastatin, pitavastatin, pravastatin, rosuvastatin, and simvastatin. Combinations of statins with another agent can be also be used. Examples include, but are not limited to, amlodipine/atorvastatin, aspirin/pravastatin, ezetimibe/simvastatin, niacin/simvastatin, lovastatin/niacin, simvastatin/sitagliptin and atorvastatin/ezetimibe. In certain embodiments, the statin is atorvastatin, lovastatin, pravastatin, rosuvastatin or simvastatin.

Fibrates or Fibric Acid Derivatives.

Examples include, but are not limited to, fenofibrate, gemfibrozil, bezafibrate, ciprofibrate, clinofibrate and clofibrate.

Niacin (or Nicotinic Acid).

Bile Acid Sequestrants.

Examples include, but are not limited to, cholestyramine, colesevelam, colestilan and colestipol.

Ezetimibe, Lomitapide, Phytosterols or Orlistat.

PCSK9 Inhibitors.

Examples include, but are not limited to, alirocumab and evolocumab.

4. Neprilysin inhibitors (also known as endopeptidase inhibitors or NEP inhibitors or enkephalinase inhibitors). For example sacubitril, or the combination of sacubitril with valsartan. Other neprilysin inhibitors in development that could be combined with Compound I include TD-1439 and TD-0714. In some embodiments, the neprilysin inhibitor is sacubitril or combinations of sacubitril with other agents.
5. Renoprotective drugs. Examples include, but are not limited to, bardoxolone, ACE inhibitors (such as captopril), ARBs (such as losartan or irbesartan), SGLT2 inhibitors (such as canagliflozin), GLP1 receptor agonists, MRAs (such as finerenone), ERAs (such as atrasentan), and apoptosis signal-regulating kinase 1 (ASK1) inhibitors (such as selonsertib).

EXAMPLES

For this invention to be better understood, the following examples are set forth. These examples are for purposes of illustration only and are not be construed as limiting the scope of the invention in any manner. All references provided in the Examples are herein incorporated by reference.

Example 1

A Multicenter, Randomized, Double-Blind, Placebo-Controlled, Phase2 Study to Evaluate the Safety and Efficacy of IW-1973 in Patients with Type 2 Diabetes with Albuminuria Treated with Renin-Angiotensin System Inhibitors List of Abbreviations and Definition of Terms ABPM ambulatory blood pressure monitoring
ACEi angiotensin-converting enzyme inhibitor
AE adverse event
ALT alanine aminotransferase
AOBP automated office blood pressure
ARB angiotensin receptor blocker
AST aspartate aminotransferase
AUC area under the plasma concentration time curve
BID twice daily
BMI body mass index (kg/m2)
BP blood pressure
BUN blood urea nitrogen.
CBC complete blood count
cGMP cyclic guanosine 3',5'-monophosphate
CKD-EPI Chronic Kidney Disease Epidemiology Collaboration
CL/F apparent systemic clearance after oral dosing CMH Cochran-Mantel-Haenszel
CYP3A cytochrome P450 3A
DBP diastolic blood pressure
DMC Data Monitoring Committee
DN diabetic nephropathy
DNA deoxyribonucleic acid
ECG electrocardiogram
eCRF electronic case report form
EDC electronic data capture
eGFR estimated glomerular filtration rate (mL/min/1.73 m2)
eNOS endothelial nitric oxide synthase
EQ-5D-5L EuroQOL 5-dimension questionnaire
ESRD end-stage renal disease
FDA Food and Drug Administration
FPG fasting plasma glucose
FPI fasting plasma insulin
GCP good clinical practice
GGT gamma glutamyl transferase
GI gastrointestinal
GLP good laboratory practice
h hour(s)
HbA1c hemoglobin A1c (glycated hemoglobin)
HBSAG hepatitis B surface antigen
HCV hepatitis C virus
HDPE high-density polyethylene
hERG ether-à-go-go related gene
HIV human immunodeficiency virus
HOMA-IR homeostatic model assessment to quantify insulin resistance HPF high power field
HR heart rate
$IC_{50}$ half maximal inhibitory concentration
ICF informed consent form
ICH International Conference on Harmonisation
IRB Institutional Review Board
ITT intent to treat
IUD intrauterine device
IWRS interactive web response system
KDIGO Kidney Disease: Improving Global Outcomes
KDQOL-SF Kidney Disease Quality of Life-Short Form
kg kilogram
kg/m2 kilograms/meters squared (body mass index)
LDH lactate dehydrogenase
L-NAME L-nitroarginine methyl ester
LS least square
m minute
MAD multiple ascending dose
MAP mean arterial pressure.

MCH mean corpuscular hemoglobin
MCHC mean corpuscular hemoglobin concentration
MCV mean corpuscular volume
MedDRA Medical Dictionary for Regulatory Activities
MEMS Medication Event Monitoring System
mg milligram
MI myocardial infarction
mL milliliter
mm Hg millimeters of mercury
MMRM mixed-effects model repeated measures
MPV mean platelet volume
msec millisecond
NO nitric oxide
NT-proBNP N-terminal pro B-type natriuretic peptide
NYHA New York Heart Association
PEG polyethylene glycol
pd postdose
PD pharmacodynamic(s)
PDE phosphodiesterase
PGIC Patient Global Assessment of Change
PGIS Patient Global Assessment of Severity
PID patient identification
PK pharmacokinetic(s)
PKG protein kinase G
PP per protocol
PRN pro re nata [ie, as needed]
PT preferred term
QD once daily
QTcF QT interval corrected using Fridericia's formula
RAAS renin-angiotensin-aldosterone system
SAE serious adverse event
SBP systolic blood pressure
Scr serum creatinine
sGC soluble guanylate cyclase
SOC system organ class
tau dosing interval
TEAE treatment-emergent adverse event
UACR urine albumin creatinine ratio Outcome Measures The primary objectives of this clinical study (Clinical Trials.gov Identifier NCT03217591) were to assess the safety and tolerability and to evaluate the effect of oral IW-1973 on renal function when administered daily for approximately 12 weeks to adult patients with type 2 diabetes mellitus with albuminuria who were on a stable regimen of renin-angiotensin system inhibitors (ERAs or ARBs).

The primary safety and tolerability measure was the incidence of Treatment-Emergent Adverse Events (TEAEs) and Study Drug-Related TEAEs.

The primary efficacy endpoint of this trial was the change from baseline in Urine Albumin to Creatinine Ratio (UACR) at Weeks 8 and 12. UACR was determined as the concentration of urine albumin [mg/dL] divided by the concentration of urine creatinine [g/dL]) from urinalysis. First morning void urine samples were collected. To reduce variability, the measurement of UACR was the average of 2-first morning void tests at each timepoint.

Other secondary objectives of this clinical study included the evaluation of the pharmacokinetic (PK) concentrations of oral IW-1973 and the exploration of the effect of oral IW-1973 on hemodynamics and metabolic effects when administered daily for approximately 12 weeks to adult patients with type 2 diabetes mellitus with albuminuria (i.e., DN patients) who were on a stable regimen of renin-angiotensin system inhibitors (RAAS inhibitors, i.e., ACEi's and ARBs).

Clinical laboratory assessments obtained during the performance of this clinical trial included: complete blood count, serum chemistry panel, urinalysis, coagulation panel, estimated glomerular filtration rate (eGFR; determined by the Chronic Kidney Disease Epidemiology Collaboration, [CKD-EPI] creatinine equation), hemoglobin A1c (HbA1C), Homeostatic Model Assessment to estimate insulin resistance (HOMA-IR), platelet function assessment (using VerifyNow®, at a subset of sites), urine pregnancy, and screens for hepatitis, human immunodeficiency virus, and drugs of abuse.

Hemodynamic and vital signs that were measure included seated and standing BP (systolic and diastolic) and pulse measurements by automated office blood pressure (AOBP), ambulatory BP (systolic and diastolic) and pulse monitoring, respiratory rate, oral temperature. Orthostatic (standing minus seated) measurements were calculated for BPs and pulse.

Biomarkers that were measured included plasma and/or serum blood and urine levels of signaling molecules. They were assessed by either LC-MS/MS, ELISA or MSD multiplex assays.

Other measurements that were taken during the performance of this trial included adverse-event recording, electrocardiograms (ECGs), physical examinations, recording of concomitant medications.

Plasma IW-1973 concentrations were measured for pharmacokinetic determinations. Plasma concentrations were consistent with previous studies, displaying dose-proportional exposure and steady state was achieved within the first 4 weeks of treatment.

The population PK approach based on sparse PK data was used to determine exposure (AUC) and oral clearance (CL/F) of IW-1973. Influence of patient demographics (eg, age, race) on exposure was evaluated. In addition, exposure-effect (such as hemodynamic, exploratory biomarkers, efficacy, and safety parameters) relationships were explored. Effects of concomitant medications on IW-1973 PK was also evaluated.

Praliciguat concentrations were measured using a validated liquid chromatography tandem mass spectrometry method, as previously described (Hanrahan J P, et al. "A Randomized, Placebo-Controlled, Multiple-Ascending-Dose Study to Assess the Safety, Tolerability, Pharmacokinetics, and Pharmacodynamics of the Soluble Guanylate Cyclase Stimulator Praliciguat in Healthy Subjects" Clin Pharmacol Drug Dev. 2019, 8 (5): 564-575). Population PK analysis was performed using NONMEM 7.4 (Icon Development Solutions, Ellicott City, MD) to update an existing model established with data from three Phase 1 studies in healthy subjects and two phase 2a studies in patients with stable type 2 diabetes mellitus (T2D) and hypertension. The influence of patient demographics, renal function and concomitant medications on exposure were evaluated, and estimates of exposure (AUC) and oral clearance (CL/F) were determined.

Study Design:

This multicenter, randomized, double-blind, placebo-controlled, parallel-group study evaluated 2 dose levels of IW-1973 compared with placebo. The study population consisted of adult patients with type 2 diabetes mellitus, albuminuria, and impaired renal function. Patients had to have been taking antihyperglycemic medications for at least 12 weeks with their regimen being stable (ie, drug and dose) for at least 28 days before the Randomization Visit. Additionally, patients had to have been on a stable regimen of angiotensin-converting enzyme inhibitor (ACEi) or an angiotensin receptor blocker (ARB), for at least 28 days before the Randomization Visit. For more details, see Inclusion Criteria below. A total of 156 patients (approximately 50 patients per arm) were stratified by baseline estimated glomerular filtration rate (eGFR) into three groups: eGFR 30 to 45, >45 to 60, and >60 to 75 mL/min/1.73 $m^2$) and randomized approximately 1:1:1 to total daily 20 mg IW-1973, 40 mg IW-1973, or placebo.

Figure 2:
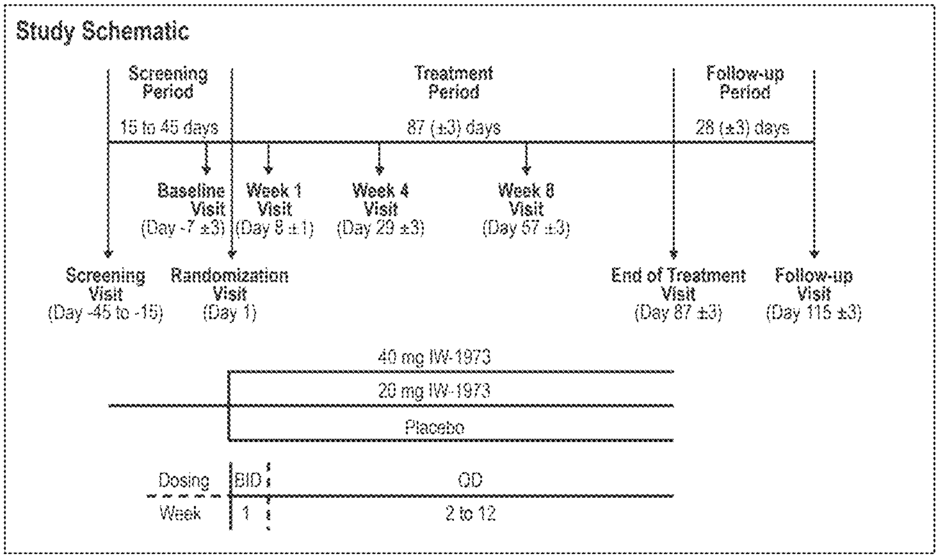
FIG. 2 is a study schematic showing three periods used in a multicenter, randomized, double-blind, placebo-controlled, parallel-group study evaluating 2 dose levels of IW-1973 compared with placebo.

The study consisted of 3 periods (see FIG. 2):

Screening Period:

The Screening Period began with the signature of the informed consent form (ICF) at the Screening Visit and lasted up to 45 days. At the Screening Visit (which could occur from Day −45 to Day −15), patients underwent preliminary screening procedures to determine their eligibility. Eligible patients returned to the clinic for the Baseline Visit (Day 7+3) for baseline and eligibility assessments including 24-hour ambulatory blood pressure monitoring (ABPM). The end of the Screening Period coincided with the beginning of the Treatment Period.

Treatment Period:

The Treatment Period began on Day 1 at Randomization (there was no Day 0) and ended after the End of Treatment Visit on Day 87 (±3). Patients were stratified in one of three groups by baseline eGFR (ie, eGFR 30 to 45, >45 to 60, and >60 to 75 mL/min/1.73 $m^2$) and randomized in an approximate 1:1:1 ratio to receive 20 mg IW-1973, 40 mg IW-1973, or placebo for approximately 12 weeks.

Dosing on Days 1 to 7 (±1) was BID (twice daily), morning and evening; dosing on Day 8 (±1) and onward was QD (once daily), 2 tablets in the morning. At the Randomization Visit on Day 1, patients received their morning dose of study drug in the clinic and underwent safety, efficacy, and pharmacokinetic (PK) assessments, including blood and urine collections at prespecified times. Patients stayed in the clinic at least 6 hours postdose and were able to leave the clinic at the Investigator's discretion following all study procedures. At the Week 1 Visit on Day 8 (±1), patients returned to the clinic and received their first QD dose of study drug in the clinic. Patients underwent safety, efficacy, and PK assessments, including blood and urine collections at prespecified times. Patients stayed in the clinic at least 6 hours postdose and were able to leave the clinic at the Investigator's discretion following all study procedures. At the Week 4 (Day 29±3), Week 8 (Day 57+3), and End of Treatment (Day 87+3) Visits, patients returned to the clinic for study drug administration; safety, efficacy, and PK assessments; and study drug supply, if applicable.

Follow-Up Period:

The Follow-up Period began immediately after the End of Treatment Visit and lasted for 28 (±3) days. At the Follow-up Visit on Day 115 (±3), patients returned to the clinic for final study assessments.

Stopping Criteria:

If any events included in FIG. 3 were reported during the study and were judged to be both study drug related and a serious adverse event, individual stopping criteria or Data Monitoring Committee (DMC) review was triggered as described below. The inclusion of these AEs was based on the clinical experience with IW-1973, the prescribing information for riociguat (an FDA approved sGC stimulator), and the patient population for this study.

On an individual basis, a patient was discontinued from study drug dosing if 1 or more SAEs from the table was reported. At the Investigator's or Sponsor's discretion, any AE(s) of concern could likewise be the basis for patient discontinuation from the trial. At Study level, an independent DMC reviewed trial safety data. The committee reviewed accumulated AE data and was able to recommend trial continuation, continuation with modification, or termination. The DMC was also required to perform an ad hoc review if SAEs from the same category in the above table.

Dosage Regimens:

Two dosage regimens were studied (see Table below, summarizing the dosage regimens by week):

One week at 10 mg BID followed by 20 mg QD for the remainder of the trial, i.e., a 20 mg total daily dosage; or One week at 20 mg BID, followed by 40 mg QD for the remainder of the trial, i.e., a 40 mg total daily dosage.

| Dose | Week 1, BID Dosing | Weeks 2 through 12, QD Dosing |
|---|---|---|
| 20 mg | one 10-mg IW-1973 Tablet, orally twice daily | two 10-mg IW-1973 Tablets. orally once daily |
| 40 mg | one 20-mg IW-1973 Tablet, orally twice daily | two 20-mg IW-1973 Tablets. orally once daily |
| Placebo | one matching placebo tablet, orally twice daily | two matching placebo tablets, orally once daily |

BID = twice daily;
QD = once daily

Per Investigator discretion, on a per-patient basis, dose could be reduced by half, i.e., from 2 tablets daily to 1 tablet daily (in the morning). Each patient's dose could only be reduced once and could not be increased after reduction.

Study Drug:

Compound I was administered as multiples of a 10 mg oral tablet dosage form (10 mg dose) or multiples of a 20 mg oral tablet dosage form (40 mg dose). Placebo was administered as multiples of matching placebo tablets. Compound I was formulated as a spray dried dispersion tablet formulation as described in WO2017095697.

Study Drug Administration

Patients received daily study drug for up to 90 days. Total patient participation was between 131 and 163 days, including the Screening, Treatment, and Follow-up Periods. During Week 1, patients took study drug BID (2×/day), 1 tablet in the morning and 1 tablet approximately 12 hours later in the evening, preferably at approximately the same times each day. From the Week 1 Visit (Day 8+1) on, patients took study drug QD (1×/day), 2 tablets in the morning, preferably at approximately the same time each day. Patients were instructed to take study drug with water, with or without food.

Inclusion Criteria:

Patients had to meet all of the following criteria to be eligible for enrollment in this study:

1. Patient has signed an informed consent form (ICF) before any study-specific procedures are performed.
2. Patient is an ambulatory male or female from 25 to 75 years old at the Screening Visit.
3. Patient has type 2 diabetes diagnosed by a physician or nurse practitioner ≥6 months before the Screening Visit, has been on ≥1 antihyperglycemic medication for ≥12 weeks preceding the Randomization Visit, and has been on a stable regimen (i.e., same drug and same dose) of ≥1 antihyperglycemic medication for ≥28 days preceding the Randomization Visit. (Modification of short-acting insulin throughout the Screening Period did not affect eligibility.)

4. Patient has been on a stable regimen (i.e., same drug and dose) of an angiotensin-converting enzyme inhibitor (ACEi) or an angiotensin receptor blocker (ARB), for ≥28 days preceding the Randomization Visit and is expected to remain on their regimen through the Follow-up Visit. (Note: These medications were allowed to be modified during the study if medically necessary.)
5. If patient is on medications for hypertension, regimen (drug[s] and dose[s]) must be stable for ≥28 days preceding the Randomization Visit and is expected to remain stable through the Follow-up Visit. (Note: Medications for antihypertension were allowed to be modified during the study if medically necessary.)
6. Patient has the following:
a. Estimated glomerular filtration rate (eGFR) 30 to 75 mL/min/1.73 m2 by the Chronic Kidney Disease Epidemiology Collaboration (CKD-EPI) creatinine equation at the Screening and Baseline Visits.
b. Urine albumin creatinine ratio (UACR)>200 mg/g and <5000 mg/g at the Screening and Baseline Visits (at the Baseline Visit, the mean of the 2 first morning void tests will be used to determine eligibility)
c. Serum albumin >3.0 g/dL at the Screening and Baseline Visits
d. Hemoglobin A1c (HbA1c)≤12% at the Screening and Baseline Visits
e. Systolic blood pressure (BP) of 110 to 160 mm Hg based on the average of 3 seated automated office blood pressure (AOBP) measurements at the Screening and Baseline Visits.
7. Female patient must be postmenopausal (no menses for ≥12 consecutive months); surgically sterile (ie, bilateral oophorectomy, hysterectomy, or tubal sterilization [tie, clip, band, or burn]); must agree to completely abstain from heterosexual intercourse; or, if heterosexually active, must agree to use 1 of the proposed methods of birth control from the date she signs
8. Male patients must be surgically sterile by vasectomy (conducted ≥60 days before the Screening Visit or confirmed via sperm analysis), must agree to completely abstain from heterosexual intercourse, or, if heterosexually active, must agree to use a combination of 2 highly effective birth control methods from the Screening Visit through 60 days after the final dose of study drug.
9. Patient must agree not to make any major lifestyle (eg, diet, exercise) changes from the Screening Visit through the Follow-up Visit.

Exclusion Criteria:

Patients who met any of the following criteria were not be eligible to participate in the study:

1. Patient has a history of secondary hypertension (ie, renal artery stenosis, primary aldosteronism, or pheochromocytoma).
2. Patient has a body mass index (BMI)<20 or >45 kg/$m^2$ at the Screening Visit.
3. Patient has elevated (>1.5x the upper limit of normal as defined by laboratory) levels of alanine aminotransferase (ALT) or aspartate aminotransferase (AST) at the Screening or Baseline Visits.
4. Patient has hemoglobin level <9 g/dL at the Screening or Baseline Visit.
5. Patient has a 12-lead electrocardiogram (ECG) demonstrating severe bradycardia (heart rate <50 beats per minute) or QTcF is >450 msec for male patients or is ≥470 msec for female patients at the Screening or Baseline Visit. (NOTE: If on initial ECG, QTcF exceeded the limit, the ECG was repeated 2 more times, and the average of the 3 QTcF values was used to determine the patient's eligibility at the Screening and Baseline Visits.)
6. Patient has "any history of platelet dysfunction, hemophilia, von Willebrand disease, coagulation disorder, other bleeding diathesis, or significant, nontraumatic bleeding episodes, such as from a gastrointestinal (GI) source.
7. Patient has hepatic impairment defined as Child-Pugh A, B, C.
8. Patient has significant comorbidities (eg, malignancy, advanced liver disease, pulmonary hypertension, pulmonary fibrosis, lung disease requiring supplemental oxygen) or other significant conditions, including clinically significant abnormality(ies) in laboratory values, that, in the Investigator's opinion, would limit the patient's ability to complete or participate in this clinical study; has been hospitalized for cardiovascular, renal, or metabolic cause in the 3 months before the Screening Visit; or has a life expectancy of less than 1 year.
9. Patient has a history of a chronic GI disease, which in the Investigator's opinion could cause significant GI malabsorption.
10. Patient with known nondiabetic renal disease (eg, known polycystic kidney disease, focal segmental glomerulosclerosis or FSGS) or nondiabetic etiology of renal function compromise. Concomitant hypertension-associated nephrosclerosis superimposed on diabetic nephropathy is acceptable.
11. Patient has had prior dialysis, renal transplant, or planned renal transplant. (Prior dialysis does not include transient, short-term dialysis indicated for an illness or during acute hospitalization. This: "transient" dialysis must have occurred >3 months prior to Randomization, must have been <7 days in duration, and the current eGFR must be stable and within the eligible range [>30 mL/min/1.73 $m^2$].)
12. Patient has clinically active, symptomatic, or unstable coronary artery or heart disease within the 3 months before the Screening Visit, defined as 1 of the following: a. Hospitalization for myocardial infarction (MI), unstable angina, or heart failure. b. New-onset angina with positive functional study or coronary angiogram revealing stenosis c. Coronary revascularization procedure
13. Patient has a documented history of New York Heart Association (NYHA) Class III or IV heart failure. A prior brief/transient NYHA Class III or IV designation is not exclusionary provided that, at Randomization, the status is Class II or better and has been stable without deterioration into a more severe class for ≥3 months.
14. Patient has a positive hepatitis panel (hepatitis B. surface antigen [HBsAg] and antihepatitis C virus [HCV]) or human immunodeficiency virus (HIV) antibody at the Screening Visit.
15. Patient has a history of viral or bacterial infection within 4 weeks of the Screening Visit.

16. Patient has had surgery with general anesthesia in the 12 weeks before the Screening Visit or has scheduled or planned surgery with general anesthesia during the study.
17. Patient has a history of active alcoholism or drug addiction during the year before the Screening Visit or, at the Screening Visit, has a positive drug screen for drugs not legally prescribed.
18. Patient is taking specific inhibitors of phosphodiesterase 5 (PDE5), nonspecific inhibitors of PDE5 (including dipyridamole and theophylline), any supplements for the treatment of erectile dysfunction, riociguat, or nitrates or nitric oxide (NO) donors in any form. These medications and supplements are prohibited from 7 days before Randomization through the duration of the study.

Patient is taking strong cytochrome P450 3A (CYP3A) inhibitors, examples of which include azole antifungals, macrolide antibiotics, protease inhibitors, and diltiazem. These medications and excessive grapefruit intake are prohibited 14 days before Randomization through the duration of the trial.

19. Female patient who may wish to become pregnant and/or plan to undergo egg donation or egg harvesting for current or future in vitro fertilization during the study and for at least 60 days after the final dose of study drug.
24. Patient will not be able to adhere to the trial assessment schedule, or, in the clinical judgment of the Investigator, the patient is otherwise not suitable for the trial.

Study Population/Demographics 156 patients were enrolled in this trial, 54 received placebo, 50 received a total oral daily dose of 20 mg and 52 received a total oral daily dose of 40 mg. Overall, between 81% and 94% of the patients completed the trial depending on the arm. The median age of patients receiving the drug was 66 years old. About 65% of the patients receiving the drug were male. About 70% of the patients that received the drug were white and 30% where black. About 60% of the white patients were of latino ethnicity. The median BMI of patients receiving the drug was 32.5.

Table 1 below summarizes the study population by race, ethnicity, BMI, and weight. The study population had significant representation of Blacks/African Americans, a population that is disproportionately affected by type 2 diabetes mellitus and nephropathy compared to the general population. There was a significant representation of Latino participants as well. The population had a median age in the mid-60s, was predominantly male, and had a median BMI in the low 30s, characteristics typical of the larger DKD population and of other Phase 2 studies in this indication.

TABLE 1

Demographics (ITT Population): Balanced Across Groups

| Variable | Subgroup | Placebo (N = 54) | PRL 20 mg (N = 50) | PRL 40 mg (N = 52) | PRL Combined (N = 102) |
|---|---|---|---|---|---|
| Age (years), median | | 66 | 65 | 66 | 66 |
| Sex, n (% Male) | | 37 (69%) | 34 (68%) | 32 (62%) | 66 (65%) |
| Race, n (%) | White | 41 (76%) | 33 (66%) | 37 (71%) | 70 (69%) |
| | Black | 10 (19%) | 13 (26%) | 14 (27%) | 27 (27%) |
| | Other | 3 (6%) | 4 (8%) | 1 (2%) | 5 (5%) |
| Ethnicity, n (%) | Latino | 25 (46%) | 30 (60%) | 30 (58%) | 60 (59%) |
| | Not Latino . . . | 29 (54%) | 20 (40%) | 22 (43%) | 42 (41%) |
| Weight (kg), median | | 93.4 | 90.1 | 94.9 | 92.1 |
| BMI ($kg/m^2$), median | | 32.1 | 32.1 | 33.6 | 32.5 |

BMI = body mass index;
PRL = praliciguat.

20. Male patient unwilling to refrain from sperm donation during the study and for at least 60 days after the final dose of study drug.
21. Patient has a history of clinically significant hypersensitivity or allergies to any of the inactive ingredients contained in the active or placebo drug products.
22. Patient has previously received Compound I in a study, or received an investigational drug during the 30 days or 5 half-lives of that investigational drug (whichever is longer) before the Screening Visit, or is planning to receive another investigational drug at any time during the study.
23. Female patient is pregnant or nursing at the Screening Visit. Nursing is not allowed from the Screening Visit through the Follow-up Visit.

The remaining baseline demographic characteristics of the population enrolled in the trial is summarized in FIG. 4.

Concomitant Drugs/Combination Therapy

At baseline, per protocol, all participants were on a stable regimen of an ACEi or an ARB and at least 1 antihyperglycemic medication. In addition, most participants were also on stable medical regimens for blood pressure and lipid control, consistent with current standard of care. These participants represented a real-world population with >71% of participants on ≥5 of these standard-of-care medications. The table below provides a summary of the concomitant medications patients were on at baseline:

| Concomitant Medications at Baseline | | | |
|---|---|---|---|
| Antihyperglycemic Drugs | | Cardiovascular Drugs | |
| Drug/Class | Baseline Use (Overall) | Drug/Class | Baseline Use (Overall) |
| Insulin | 64% | ACE/ARB | 100%; eligibility criterion |
| Metformin | 42% | Statins | 75% |
| Sulfonylureas | 26% | Calcium channel blockers | 52% |
| GLP1 agonists | 15% | Diuretics | 39% |
| DPP4 inhibitors | 14% | Beta blockers | 53% |
| SGLT2 inhibitors | 7% | Alpha blockers | 30% |
| Thiazolidinediones | 5% | Platelet Inhibitors | 60% |

ACE = angiotensin-converting enzyme;
ARB = angiotensin II-receptor blocker;
DPP4 = Dipeptidyl peptidase 4;
GLP1 = glycogen-line peptide 1:
SGLT2 = sodium glucose co-transporter 2.

Top-Line Assessments/Results

A) Intention-to-Treat (ITT) Population

Primary Efficacy Endpoint:

For the primary efficacy endpoint, there was a trend for praliciguat to reduce UACR over 12 weeks, with a 28% reduction from baseline in the combined praliciguat groups and 15% placebo-adjusted reduction from baseline. The trend vs. placebo did not attain statistical significance. Similar reductions in UACR were seen in the 20-mg and 40-mg praliciguat dose groups. Effects on albuminuria as measured by UACR changes are summarized in FIG. 5 (combined results of weeks 8 and 12).

Figure 1B:
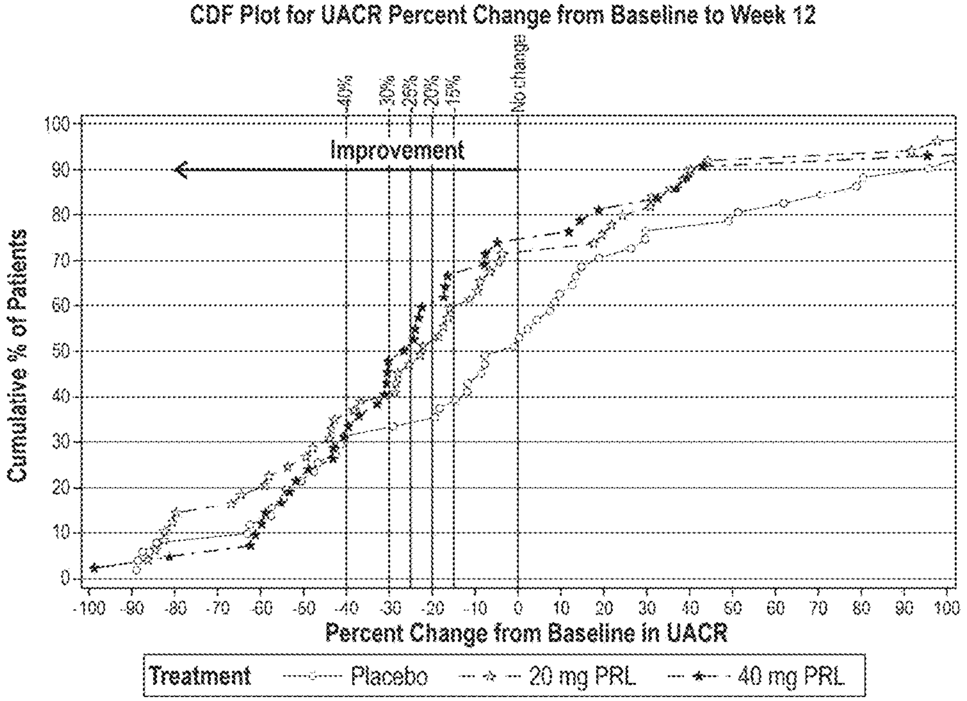

FIG. 6 summarizes the results for changes at week 12:

FIGS. 1A and 1B display the results for the primary efficacy outcome measure (change in UACR) in two populations: FIG. 1A shows the results for a subpopulation of patients with eGFR between 30 and 45 mL/min/1.73 $m^2$ and FIG. 1B shows the results for all patients. As can be seen by comparing the two figures, at week 12, the group of patients with lower levels of eGFR (i.e., the patients with more impaired kidney function) display a more pronounced effect both versus baseline and as compared to placebo.

Other subgroups of populations showed trends towards improved response in responder analysis include: males, patients of non-Hispanic ethnicity, patients with BMI $<30$ and patients with mean arterial pressure (MAP) below the median for the specific cohort.

Blood Pressure/Hemodynamic Effects:

Praliciguat treatment was associated with a consistent decline in average 24-hour blood pressure after 12 weeks of treatment. An average change between −3.2 and −4.0 mmHg in MAP versus placebo was observed for the different cohorts in this trial. An average change between −4.0 and −4.4 mm Hg in systolic blood pressure was observed for the different cohorts in this trial. These differences were statistically significant. These results are summarized in FIGS. 7 and 8.

Mediation analysis suggested that about ⅔ or more of the effect observed on UACR is independent of blood pressure changes and cannot be explained by those.

Metabolic Outcomes:

Improvements on several metabolic parameters were observed in this trial. Praliciguat treatment for 12 weeks was associated with a ~0.3% decrease in mean HbA1c levels compared to placebo, suggesting improved glycemic control in patients with type 2 diabetes and diabetic kidney disease. Praliciguat treatment was also associated with modest declines in mean serum cholesterol and LDL cholesterol over 12 weeks, compared to placebo. Overall positive metabolic outcomes include reduction of fasting plasma glucose, reduction in HbA1C, reduction in total serum cholesterol and serum LDL cholesterol. These results are. summarized in FIGS. 9-12.

B) Identification of mITT Population

During routine data validation, 1 site (with 23 randomized study participants) was flagged for multiple anomalies.

First, as predefined in the Statistical Analysis Plan (SAP), BQL (below quantification level) values for praliciguat in plasma at Weeks 8 and 12 in praliciguat-treated participants were flagged as major protocol deviations; the site was noted as having the highest incidence of such cases.

Second, during data verification, inspection of interactions between treatment, visit, and geographic region showed the Southeast US region separated out from the rest of the regions, and furthermore, this regional difference was entirely driven by data from this site.

Third, during topline data quality checks, increasing variability in the data at later study visits was noted; further investigation uncovered this site was a major contributor to this variability.

Participants from this site had an improbable frequency of high responders. There were 13 high responders in the study overall. Of these 13 high responders, 9 were from this site—6 of those received praliciguat but only 2 had expected drug concentrations. In contrast, the 4 other high responders were from the remaining 42 sites in the study. The likelihood that such a disproportionate occurrence of high responders could occur among the 23 site participants by chance is less than 1 in 10,000.

Based on the much larger-than-expected proportion of high responders from this site, combined with little-to-no plasma drug concentrations, it was believed that analyses based on the ITT Population with this site's participants removed-herein termed the mITT Population (or modified intention-to-treat population)-provides a better estimate of the effects of praliciguat in this study, Analysis of either the mITT or ITT Population shows reduction in UACR and improvements in key cardiovascular risk factors.

UACR: Mean Percent Change from Baseline Over Weeks 8 and 12 (mITT Population and ITT Population)

The primary efficacy analysis of mean percent change from baseline in UACR over Weeks 8 and 12 is summarized for the mITT and ITT Populations in the table below. In the mITT Population, the placebo-adjusted mean percent decrease from baseline for the combined praliciguat treatment groups was 20% with a nominal p-value of 0.030. In the ITT Population, the placebo-adjusted mean percent decrease for the combined praliciguat treatment groups was 15% with a p-value of 0.174.

| UACR Mean % CFB at Weeks 8 & 12 | mITT Population | | | | ITT Population | | | |
|---|---|---|---|---|---|---|---|---|
| | Placebo N = 46 | PRL 20 mg N = 41 | PRL 40 mg N = 46 | PRL Combined N = 87 | Placebo N = 54 | PRL 20 mg N = 50 | PRL 40 mg N = 52 | PRL Combined N = 102 |
| Within Group (90% CI) | −4.2% (−16.7, 10.1) | −18.4% (−29.5, −5.6) | −28.3% (−38.2, −16.7) | −23.5% (−31.2, −14.8) | −14.8% (−27.7, 0.4) | −28.4% (−39.4, −15.3) | −27.3% (−39.2, −13.1) | −27.8% (−36.3, −18.3) |
| Placebo Adjusted (90% CI) | | −14.8% (−30.0, 3.8) | −25.1% (−38.6, −8.6) | −20.1% (−32.6, −5.3) | | −16.0% (−33.3, 5.8) | −14.6% (−32.7, 8.3) | −15.3% (−30.7, 3.6) |
| Nominal p-value | | 0.182 | 0.017 | 0.030 | | 0.2142 | 0.2718 | 0.1736 |

Data were analyzed using a MMRM analysis with change from baseline in log-transformed UACR as the response variable, treatment, visit, treatment-by visit interaction, and baseline eGFR stratum (using the actual stratum based on the eGFR lab values rather than the information from IRT) as fixed effects, baseline log-transformed UACR and baseline MAP as covariates, and unstructured as the variance-covariance structure. Geometric LS mean change (%) and the associated confidence intervals are derived as 100 * [exp(LS mean change) − 1].
CFB = change from baseline;
CI = confidence interval;
MMRM = mixed-effects model repeated measures;
PRL = praliciguat;
UACR = urine albumin-to-creatinine ratio.

UACR: Mean Percent Change from Baseline at Week 12 (mITT Population)

For UACR at Week 12, the placebo-adjusted mean percent decrease for the combined praliciguat treatment groups was 23% with a nominal p-value of 0.07. See table below.

| UACR: Mean CFB at Weeks 8 & 12 | Placebo N = 46 | PRL 20 mg N = 41 | PRL 40 mg N = 46 | PRL Combined N = 87 |
|---|---|---|---|---|
| Within Group (90% CI) | −4.1% (−20.6, 15.7) | −24.7% (−38.2, −8.3) | −27.4% (−40.8, −10.9) | −26.1% (−36.0, −14.6) |
| Placebo Adjusted (90% CI) | | −21.5% (−40.0, 2.8) | −24.2% (−43.4, −0.4) | −22.9% (−38.9, −2.6) |
| Nominal p-value | | 0.14 | 0.10 | 0.07 |

Data were analyzed using a MMRM analysis with change from baseline in log-transformed UACR as the response variable, treatment, visit, treatment-by visit interaction, and baseline eGFR stratum as fixed effects, baseline log-transformed UACR and baseline MAP as covariates, and unstructured as the variance-covariance structure.
Geometric mean change (%) and the associated confidence intervals are derived as 100 * [exp(LS mean change) − 1].
CFB = change from baseline;
CI = confidence interval;
MMRM = mixed-effects model repeated measures;
PRL = praliciguat;
UACR = urine albumin-to-creatinine ratio.

One subgroup of particular interest is patients with greatly reduced eGFR because these patients are at greater risk for progression to ESRD. Mean percent changes from baseline in UACR over the 12-week treatment period for participants in the mITT Population stratified by baseline level of eGFR was determined. Participants with more severely (eGFR 30-45 mL/min/1.73 $m^2$) and less severely (eGFR>45 mL/min/1.73 $m^2$) decreased eGFR both had meaningful mean reductions from baseline in UACR. Interestingly, the magnitude of placebo-corrected mean reduction (30-40%) was greater in participants with a greater degree of renal compromise at baseline suggesting that praliciguat can provide meaningful clinical benefit even in more advanced stages of DKD. Importantly, praliciguat is metabolized in the liver with negligible renal excretion; this lack of renal metabolism may be particularly advantageous for this subgroup of DKD patients.

From mediation analyses, it was determined that for the mITT Population, only 4 to 17% of the total effect of treatment on change in UACR is mediated through change in systolic blood pressure. Similarly, for the ITT Population, only 8 to 25% of the total UACR change is mediated through change in systolic blood pressure. When using Week 12 trough cuff systolic blood pressure as the mediator, a more common but less comprehensive blood pressure measure, only 3% of the total UACR change is mediated through change in SBP.

Metabolic Outcomes

Consistent placebo-adjusted decreases in cholesterol and LDL cholesterol were also noted for both praliciguat dose groups in the mITT population. Notably, these improvements were evident while approximately 75% of study participants were taking standard-of-care lipid-lowering medication regimens and had median baseline total cholesterol levels of <170 mg/dL.

TABLE 2

Cholesterol and LDL Cholesterol: LS Mean (90% CI) Change from Baseline at Week 12 (mITT Population)

| Parameter | Statistic | Placebo N = 46 | PRL 20 mg N = 41 | PRL 40 mg N = 46 | PRL Combined N = 87 |
|---|---|---|---|---|---|
| Cholesterol (mg/dL) | | | | | |
| Baseline | Median | 150 | 169 | 159.5 | |
| | $25^{th}$, $75^{th}$ percentile | 128, 185 | 145.5, 169 | 133, 185 | |

TABLE 2-continued

| Cholesterol and LDL Cholesterol: LS Mean (90% CI) Change from Baseline at Week 12 (mITT Population) | | | | | |
|---|---|---|---|---|---|
| Parameter | Statistic | Placebo N = 46 | PRL 20 mg N = 41 | PRL 40 mg N = 46 | PRL Combined N = 87 |
| Analysis Result | Within Group LS Mean | 2.5 | −10.6 | −4.8 | −7.7 |
| | Change (90% CI) | (−5.8, 10.8) | (−19.5, −1.7) | (−13.6, 4.1) | (−14.2, −1.2) |
| | Placebo-Adjusted LS | | −13.1 | −7.5 | −10.2 |
| | Mean Change (90% CI) | | (−24.8, −1,4) | (−18.9, 4.3) | (−20.2, −0.2) |
| | Nominal p-value | | 0.07 | 0.30 | 0.09 |
| LDL Cholesterol (mg/dL) | | | | | |
| Baseline | Median | 70 | 86 | 79.5 | |
| | $25^{th}$, $75^{th}$ percentile | 55, 100 | 67, 122 | 56, 111 | |
| Analysis Result | Within Group LS Mean | 4.6 | −8.8 | −4.9 | −6.9 |
| | Change (90% CI) | (−2.7, 11.9) | (−16.3, −1.3) | (−12.6 2.7) | (−12.5, −1.2) |
| | Placebo Adjusted LS | | −13.4 | −9.5 | −11.4 |
| | Mean Change (90% CI) | | (−23.4, −3.4) | (−19.6, 0.6) | (−20.1, −2.8) |
| | Nominal p-value | | 0.03 | 0.12 | 0.03 |

CI = confidence interval;
PRL = praliciguat.

The invention claimed is:

1. A method of treating diabetic nephropathy (DN) in a human patient in need thereof by administering to said patient a total oral daily dose of between 20 mg and 40 mg of Compound I:

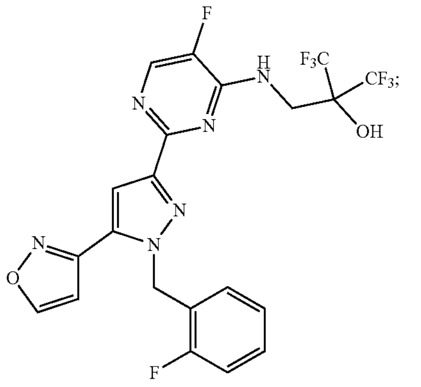 [SMILES: OC(CNc1nc(-c2cc(-c3ccon3)n(Cc3ccccc3F)n2)ncc1F)(C(F)(F)F)C(F)(F)F]

wherein the patient has an estimated glomerular filtration rate (eGFR) between 30 and 45 mL/min/1.73 $m^2$ and a urine to albumin creatinine ratio (UACR) that is higher than 200 mg/g and lower than 5000 mg/g at the start of the treatment.

2. The method of claim 1, wherein:

i) the method lowers urine to albumin creatinine ratio (UACR) of the patient;

ii) the method lowers blood pressure in the patient;

iii) the method lowers mean arterial pressure (MAP) of the patient;

iv) the method lowers systolic blood pressure of the patient;

v) the method does not result in a significant reduction in blood pressure in the patient;

vi) the method improves one or more metabolic parameters in the patient; wherein the one or more metabolic parameters are selected from fasting plasma glucose, hemoglobin A1c (HbA1c), fasting plasma insulin, HOMA-IR, serum total cholesterol, and LDL cholesterol;

vii) the method reduces the risk of cardiovascular events in the patient; or viii) the pharmaceutical composition improves metabolic outcomes in the patient.

3. A method of improving albuminuria in a diabetic human patient in need thereof by administering to said patient a total oral daily dose of between 20 mg and 40 mg of Compound I:

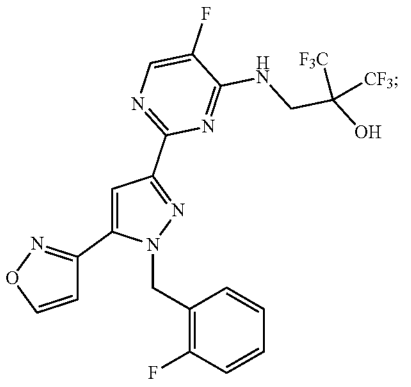 [SMILES: OC(CNc1nc(-c2cc(-c3ccon3)n(Cc3ccccc3F)n2)ncc1F)(C(F)(F)F)C(F)(F)F]

wherein the patient has an estimated glomerular filtration rate (eGFR) between 30 and 45 mL/min/1.73 $m^2$ and a urine to albumin creatinine ratio (UACR) that is higher than 200 mg/g and lower than 5000 mg/g at the start of the treatment.

4. The method of claim 3, wherein the method lowers urine to albumin creatinine ratio (UACR) of the patient.

5. The method of claim 3, wherein the method does not result in significant reduction in blood pressure of the patient.

6. The method of claim 3, wherein the patient is taking a GLP-1 inhibitor for glycemic control.

7. The method of claim 1, wherein:

i) the method preserves renal function in the patient;

ii) the method delays or prevents clinical worsening in the patient; and/or iii) the method increases survival in the patient.

8. The method of claim 1, wherein:

i) a total oral daily dose of between 20 mg and 30 mg of Compound I is administered to said patient; or ii) an oral daily dose of between 30 mg and 40 mg of Compound I is administered to said patient.

9. The method of claim 1, wherein:

i) the patient is administered a single oral daily dose of 20 mg of Compound I;

ii) the patient is administered a single oral daily dose of 25 mg of Compound I;

iii) the patient is administered a single oral daily dose of 30 mg of Compound I; or iv) the patient is administered a single oral daily dose of 40 mg of Compound I.

10. The method of claim 1, wherein:

i) the patient is administered an oral dose of 10 mg of Compound I twice a day; wherein the patient is administered a first oral dose of 10 mg of Compound I and a second oral dose of 10 mg of Compound I, wherein the first dose and the second dose are separated by 5 hours to 15 hours;

ii) the patient is administered an oral dose of 12.5 mg of Compound I twice a day; wherein the patient is administered a first oral dose of 12.5 mg of Compound I and a second oral dose of 12.5 mg of Compound I, wherein the first dose and the second dose are separated by 5 hours to 15 hours;

iii) the patient is administered an oral dose of 15 mg of Compound I twice a day; wherein the patient a first oral dose of 15 mg of Compound I and a second oral dose of 15 mg of Compound I, wherein the first dose and the second dose are separated by 5 hours to 15 hours; or iv) the patient is administered an oral dose of 20 mg of Compound I twice a day; wherein the patient is administered a first oral dose of 20 mg of Compound I and a second oral dose of 20 mg of Compound I, wherein the first dose and the second dose are separated by 5 hours to 15 hours.

11. The method of claim 1, wherein:

i) the method comprises administering to the patient an initial oral dose of 10 mg twice per day for a period between 7 and 14 days; and subsequently administering to the patient a maintenance dose of 20 mg once per day;

ii) the method comprises administering to the patient an initial oral dose of 12.5 mg twice per day for a period between 7 and 14 days; and subsequently administering to the patient a maintenance dose of 25 mg once per day;

iii) the method comprises administering to the patient an initial oral dose of 15 mg twice per day for a period between 7 and 14 days; and subsequently administering to the patient a maintenance dose of 30 mg once per day; or iv) the method comprises administering to the patient an initial oral dose of 20 mg twice per day for a period between 7 and 14 days; and subsequently administering to the patient a maintenance dose of 40 mg once per day.

12. The method of claim 1, wherein:

i) the method further comprises administering to the patient one or more anti-hypertensive medications; wherein the one or more anti-hypertensive medications are independently selected from an angiotensin-converting enzyme (ACE) inhibitor, an angiotensin II receptor blocker (ARB), a diuretic, a calcium channel blocker, a beta blocker, a vasodilator, a central-acting agent and an aldosterone antagonist; at least one of the anti-hypertensive medications is an angiotensin-converting enzyme (ACE) inhibitor or an angiotensin II receptor blocker (ARB); at least one of the anti-hypertensive medication is selected from the group consisting of lisinopril, combination of lisinopril and hydrochlorothiazide, enalapril, and losartan; at least one of the anti-hypertensive medications is a diuretic; wherein the diuretic is selected from chlorthalidone and hydrochlorothiazide; or ii) the method further comprises administering to the patient two or more anti-hypertensive medications, wherein at least one of the anti-hypertensive medication is selected from an angiotensin-converting enzyme (ACE) inhibitor and an angiotensin II receptor blocker (ARB), and at least one of the anti-hypertensive medication is a diuretic; wherein the diuretic is selected from chlorthalidone and hydrochlorothiazide.

13. The method of claim 1, wherein the method further comprises administering to the patient one or more blood glucose lowering medications; wherein i) the one or more blood glucose lowering medications are independently selected from a biguanide, a GLP-1 receptor agonist, a SGLT2 inhibitor (alone or in combination with a SGLT1 inhibitor), and insulin therapy;

ii) at least one of the blood glucose lowering medications is a GLP-1 receptor agonist;

wherein the GLP-1 receptor agonist is semaglutide; or the GLP-1 receptor agonist is oral semaglutide;

iii) the one or more blood glucose lowering medications are independently selected from the group consisting of insulin, metformin, glyburide, glipizide, glimepiride, repaglinide, nateglinide, sitagliptin, saxagliptin, linagliptin, exenatide, liraglutide, semaglutide, empagliflozin, canagliflozin, and dapagliflozin; or iv) at least one of the blood glucose lowering medications is a SGLT2 inhibitor; wherein the SGLT2 inhibitor is selected from empagliflozin, canagliflozin and dapagliflozin.

14. The method of claim 1, wherein:

i) the method further comprises administering to the patient one or more anti-hypertensive medications and one or more blood glucose lowering medications; or ii) the method further comprises administering to the patient one or more anti-hypertensive medications independently selected from the group consisting of lisinopril, combination of lisinopril and hydrochlorothiazide, enalapril, losartan, chlorthalidone, metoprolol, and spironolactone and one or more blood glucose lowering medications independently selected from the group consisting of insulin, metformin, glyburide, glipizide, glimepiride, repaglinide, nateglinide, sitagliptin, saxagliptin, linagliptin, exenatide, liraglutide, semaglutide, empagliflozin, canagliflozin, and dapagliflozin.

15. The method of claim 1, wherein the method further comprises administering to the patient one or more anti-hyperlipidemic medications; wherein i) the one or more anti-hyperlipidemic medications is a cholesterol lowering medication;

wherein the one or more cholesterol lowering medications are independently selected from the group consisting of atorvastin, pravastatin, rosuvastatin, lovastatin and simvastatin; or ii) the one or more anti-hyperlipidemic medications are independently selected from the group consisting of atorvastin, pravastatin, simvastatin, rosuvastatin, lovastatin and nicotinic acid.

16. The method of claim 1, wherein:

i) the method further comprises administering to the patient one or more neprilysin inhibitors; wherein the neprilysin inhibitor is sacubitril or the combination of sacubitril with valsartan; or ii) the method further comprises administering to the patient one or more renoprotective medications; wherein the renoprotective medications is selected from the group consisting of bardoxolone, irbesartan, losartan, captopril, finerenone, canagliflozin, and atrasentan.

17. The method of claim 1, wherein:

i) the patient has a systolic blood pressure between 110 and 160 mmHg at the start of the treatment;

ii) the patient has a hemoglobin A1c level between 6.5% and 12% at the start of the treatment; or iii) the patient has a serum albumin level greater than 3.0 g/dL at the start of the treatment.

18. The method of claim 13, wherein at least one of the blood glucose lowering medications is a SGLT2 inhibitor; wherein the SGLT2 inhibitor is selected from empagliflozin, canagliflozin and dapagliflozin.

* * * * *